(12) United States Patent
Hudlicky et al.

(10) Patent No.: US 8,703,792 B2
(45) Date of Patent: Apr. 22, 2014

(54) C-1 ANALOGS OF PANCRATISTATIN AND 7-DEOXYPANCRATISTATIN AND PROCESSES FOR THEIR PREPARATION

(75) Inventors: Tomas Hudlicky, St. Catharines (CA); Jonathan Collins, Parkersburg, WV (US)

(73) Assignee: Brock University, St. Catharines (CA)

( * ) Notice: Subject to any disclaimer, the term of this patent is extended or adjusted under 35 U.S.C. 154(b) by 140 days.

(21) Appl. No.: 13/140,209

(22) PCT Filed: Dec. 17, 2009

(86) PCT No.: PCT/CA2009/001828
§ 371 (c)(1),
(2), (4) Date: Sep. 1, 2011

(87) PCT Pub. No.: WO2010/069054
PCT Pub. Date: Jun. 24, 2010

(65) Prior Publication Data
US 2011/0306629 A1 Dec. 15, 2011

Related U.S. Application Data

(60) Provisional application No. 61/138,774, filed on Dec. 18, 2008.

(51) Int. Cl.
*A61K 31/4355* (2006.01)
*A61P 35/00* (2006.01)
*C07D 491/056* (2006.01)

(52) U.S. Cl.
USPC .......................................... 514/287; 546/65

(58) Field of Classification Search
None
See application file for complete search history.

(56) References Cited

FOREIGN PATENT DOCUMENTS

WO  2008/043846 A2  4/2008
WO  2010/012714 A1  2/2010

OTHER PUBLICATIONS

Collins et al. Total synthesis of 7-deoxypancrastatin-1-carboxaldehyde and carboxylic acid via solvent-free intramolecular aziridine opening: phenanthrene to phenathridone cyclization strategy. Organic Letters, vol. 10, No. 3, pp. 361-364, 2008.*

Collins et al., "Total Synthesis of 7-Deoxypancratistatin-1-carboxaldehyde and Carboxylic Acid via Solvent-Free Intramolecular Aziridene Opening: Phenanthrene to Phenanthridone Cyclization Strategy", Organic Letters, Dec. 29, 2007 (published on web), pp. 361-364, vol. 10, No. 3, American Chemical Society.

Declaration of Dr. Jonathan Collins regarding: "Total Synthesis of 7-Deoxypancratistatin-1-Carboxaldehyde and Carboxylic Acid Via Solvent-Free Intramolecular Aziridine Opening" (Poster Presentation), Nov. 2007, Quebec-Ontario Minisymposium in Synthetic and Biological Chemistry (QOMSBOC), Montreal, Canada.

"Total synthesis and biological evaluation of Amaryllidaceae alkaloids: trans-dihydrolycoricidine, 7-deoxypancratistatin, and C-1 analogs of 7-deoxypancratistatin", (Oral Presentation), May 2009, 92nd Canadian Chemistry Conference and Exhibition (CSC), Hamilton, Canada.

"Total Synthesis of Natural Products via Chemoenzymatic and/or Reagent-Based Strategies: The Story of Morphine, Pancratistatin, and Balanol" Oral Presentation (invited), Mar. 2009, Allegheny College Chemistry Lecture Series, Meadville, PA, USA.

Collins et al. "Total Synthesis of C-1 Analogs of 7-Deoxypancratistatin Via Solvent-Free Intramolecular Aziridine Opening" (Poster Presentation), Aug. 2008, 14th Symposium On the Latest Trends in Organic Synthesis (LTOS), St. Catharines, Canada.

* cited by examiner

*Primary Examiner* — Brandon Fetterolf
*Assistant Examiner* — Anna Pagonakis
(74) *Attorney, Agent, or Firm* — Rothwell, Figg, Ernst & Manbeck, P.C.

(57) ABSTRACT

The present application relates to novel C-1 substituted analogues of pancratistatin and 7-dexoypancratistatin of Formula (I), pharmaceutical compositions thereof and the use of said compounds of Formula (I) in the treatment of cancer The application also relates to processes for the preparation of said compound of Formula (I) and intermediates thereof.

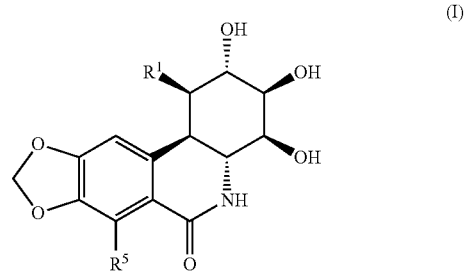

(I)

12 Claims, 3 Drawing Sheets

A)

B)

C-1 ANALOGS OF PANCRATISTATIN AND 7-DEOXYPANCRATISTATIN AND PROCESSES FOR THEIR PREPARATION

This application is a National Stage of co-pending International Application No. PCT/CA2009/001828, filed Dec. 17, 2009, which claims the benefit of Provisional Application No. 61/138,774, filed Dec. 18, 2008, the contents of both of which are herein incorporated by reference.

FIELD

The present application relates to novel C-1 analogs of pancratistatin and 7-deoxypancratistatin and to processes for their preparation. The application further relates to pharmaceutical compositions containing the novel analogs and to uses of the analogs.

BACKGROUND

Pacratistatin (1) and narciclasine (2) are natural products that are highly active against many cancer cell lines including murine P388 and lymphocytic leukemia; human cancer cells pancreas BXPC-3, breast MCF-7, CNS SF-268, lung NCI-H460, colon KM20L2 and prostate DU145. Although the exact mode of action for pancratistatin remains unknown, narciclasine is believed to inhibit peptide bond formation in eukaryotic ribosomes. Lycoricidine (3) and 7-deoxypancratistatin (4) are significantly less active, than the corresponding C-7 hydroxylated compound. The reduced activity maybe due to the absence of the hydrogen bonded donor acceptor pair in the phenanthridone functionality.

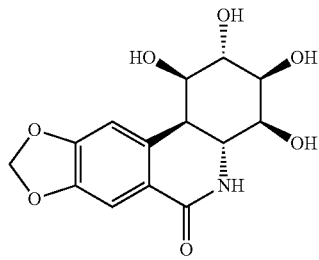

1

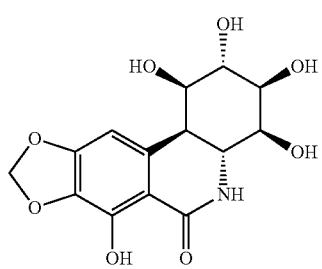

2

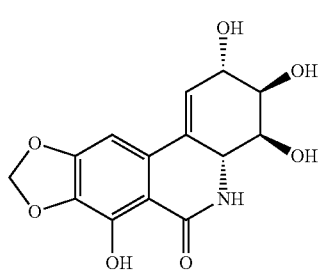

3

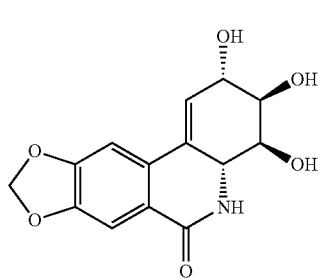

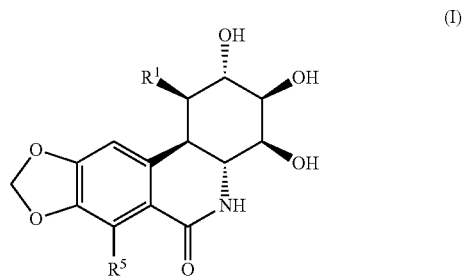

4

SUMMARY

The present application describes novel C-1 substitution analogs of pancratistatin and 7-deoxypancratistatin.

Accordingly, one aspect of the present application includes a compound of the Formula I:

(I)

wherein:

$R^1$ is selected from $C(O)R^2$, $C(O)NR^2R^3$, $CH=NR^2$, $CH_2NR^2R^3$, $CH_2OR^2$, $CH_2R^2$, $CH=CR^2R^3$, $NR^2R^3$, $NHC(O)R^2$, $NHC(O)OR^2$, $NHC(O)NR^2R^3$, $CH_2OC(O)NR^2R^3$, $CH_2NHC(O)R^2$, $CH_2NHC(O)OR^2$, $CH_2CHC(O)NR^2R^3$, $CH_2OC(O)R^2$ and $C(O)OR^4$; and $R^2$ and $R^3$ are independently selected from H, $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro;

$R^4$ is selected from $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro; and $R^5$ is selected from H and OH; and in each alkyl, alkenyl, cycloalkyl and aryl, one or more available H are optionally replaced with F, or a pharmaceutically acceptable salt, solvate or prodrug thereof.

In another embodiment, the compounds of Formula I comprise an isotopic label. Therefore the present application also includes compounds of Formula I wherein one or more atoms are replaced with an isotopic label.

In another aspect of the application there is included a pharmaceutical composition comprising one or more compounds of Formula I as defined above, and/or pharmaceutically acceptable salts, solvates and/or prodrugs thereof, and a pharmaceutically acceptable carrier.

In a further aspect of the application there is included a use of one or more compounds of Formula I as defined above, and/or pharmaceutically acceptable salts, solvates and/or prodrugs thereof, to treat cancer.

In still a further aspect of the application there is included a method of treating cancer comprising administering an effective amount of one or more compounds of Formula I as defined above, and/or pharmaceutically acceptable salts, solvates or prodrugs thereof, to a subject in need thereof.

In another aspect of the present application is a use of one or more compounds of Formula I, as defined above, and/or pharmaceutically acceptable salts, solvates and/or prodrugs thereof, as a medicament.

A further aspect of the present application is a process for the preparation of an intermediate of the Formula II:

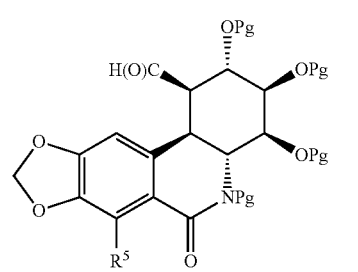

(II)

wherein $R^5$ is selected from H and OPg and each Pg may be the same or different and represent suitable protecting groups or any two adjacent Pg are joined to form a suitable cyclic protecting group;

the process comprising:

(i) reacting a compound of the Formula III with an aluminum acetylide derived from a compound of the Formula IV, followed by protection to form a compound of the Formula V, wherein $R^5$ and each Pg is as defined above:

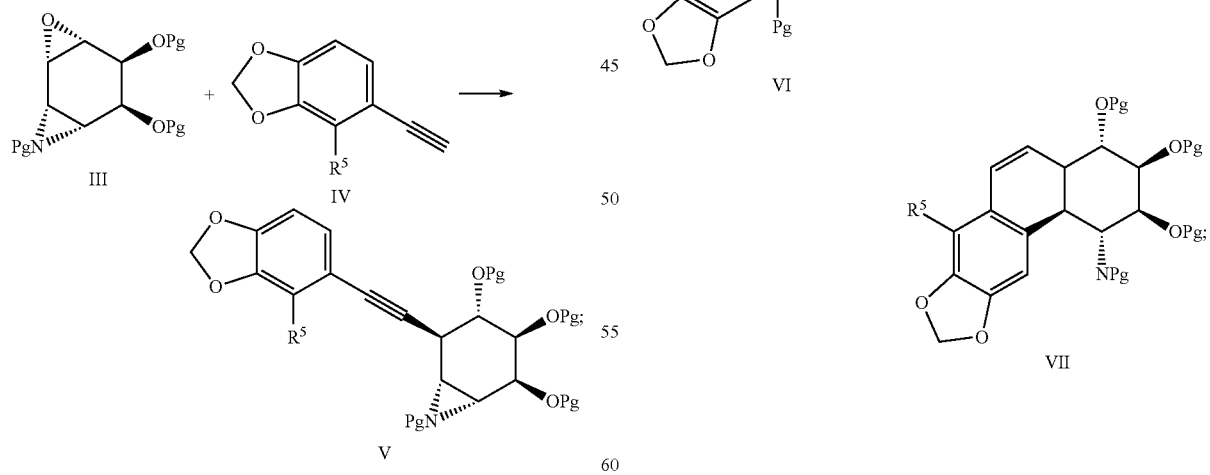

(ii) reducing the compound of Formula V to form a cis-alkene of the Formula VI, wherein $R^5$ and each Pg is as defined above:

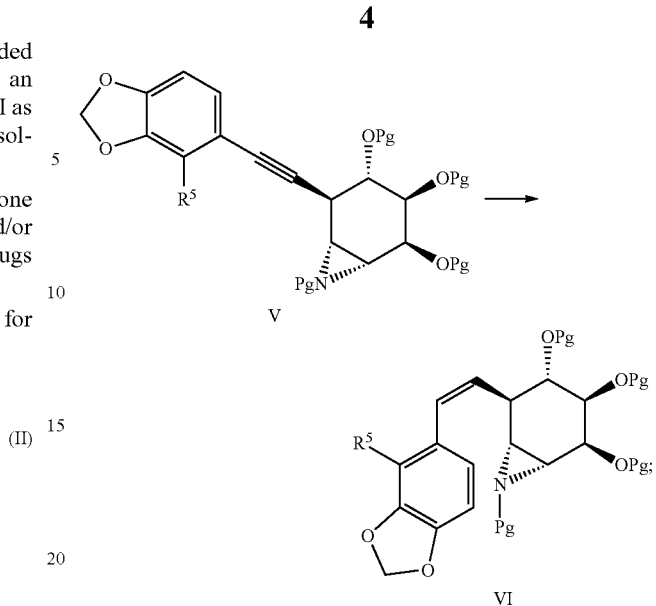

(iii) reacting the compound of the Formula VI under solid-state, silica gel catalysis conditions to form a compound of the Formula VII, wherein $R^5$ and each Pg is as defined above:

(iv) oxidatively cleaving the non-aromatic double bond in the compound of the Formula VII to form an intermediate diketone of the Formula VIII which cyclizes to form a compound of the Formula IX, wherein $R^5$ and each Pg is as defined above:

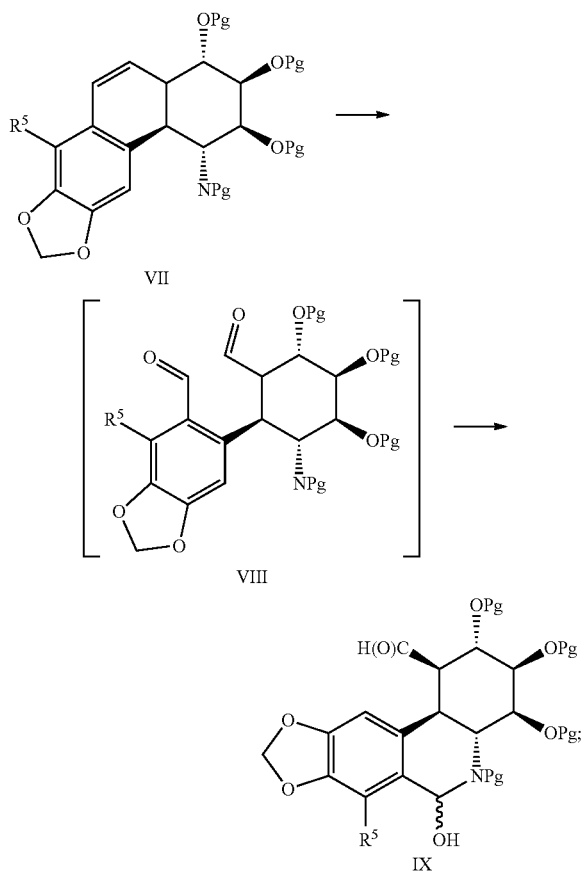

and (v) oxidizing the compound of the Formula IX to form a compound of Formula II, wherein $R^5$ and each Pg is as defined above:

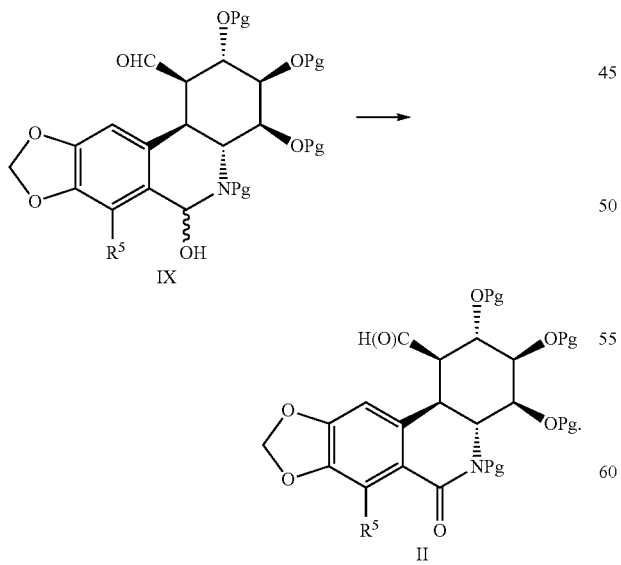

In a further aspect of the application there is included a process for preparing a compound of Formula I

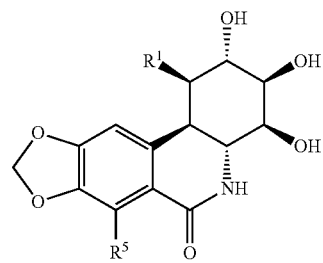

wherein:

$R^1$ is other than C(O)H and is selected from C(O)$R^2$, C(O)N$R^2R^3$, CH=N$R^2$, CH$_2$N$R^2R^3$, CH$_2$O$R^2$, CH$_2R^2$, CH=C$R^2R^3$, N$R^2R^3$, NHC(O)$R^2$, NHC(O)O$R^2$, NHC(O)N$R^2R^3$, CH$_2$OC(O)N$R^2R^3$, CH$_2$NHC(O)$R^2$, CH$_2$NHC(O)O$R^2$, CH$_2$CHC(O)N$R^2R^3$, CH$_2$OC(O)$R^2$ and C(O)O$R^4$; and $R^2$ and $R^3$ are independently selected from H, C$_{1-6}$alkyl, C$_{2-6}$alkenyl, C$_{3-10}$cycloalkyl and C$_{6-10}$aryl said latter four groups being unsubstituted or substituted with one to 5 groups independently selected from halo, OH, OC$_{1-4}$alkyl, OC(O)C$_{1-6}$alkyl and nitro;

$R^4$ is selected from C$_{1-6}$alkyl, C$_{2-6}$alkenyl, C$_{3-10}$cycloalkyl and C$_{6-10}$aryl said latter four groups being unsubstituted or substituted with one to 5 groups independently selected from halo, OH, OC$_{1-4}$alkyl, OC(O)C$_{1-6}$alkyl and nitro; and $R^5$ is selected from H and OH; and in each alkyl, alkenyl, cycloalkyl and aryl, one or more available H are optionally replaced with F, comprising:

(i) reacting a compound of the Formula II, wherein $R^5$ is selected from H and OPg and each Pg may be the same or different and represent suitable protecting groups or any two adjacent Pg are joined to form a suitable cyclic protecting group, under conditions to convert the aldehyde moiety in one or more steps to a group, other than C(O)H, selected from C(O)$R^2$, C(O)N$R^2R^3$, CH=N$R^2$, CH$_2$N$R^2R^3$, CH$_2$O$R^2$, CH$_2R^2$, CH=C$R^2R^3$, N$R^2R^3$, NHC(O)$R^2$, NHC(O)O$R^2$, NHC(O)N$R^2R^3$, CH$_2$OC(O)N$R^2R^3$, CH$_2$NHC(O)$R^2$, CH$_2$NHC(O)O$R^2$, CH$_2$CHC(O)N$R^2R^3$, CH$_2$OC(O)$R^2$ and C(O)O$R^4$, wherein $R^2$, $R^3$ and $R^4$ are as defined above, to form a compound of the Formula X wherein $R^1$, $R^5$ and each Pg are as defined above:

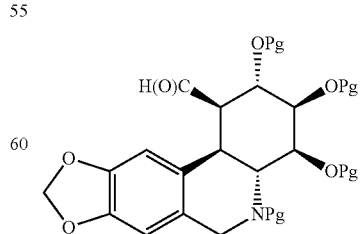

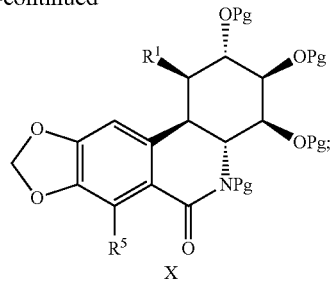

and
(ii) removing the Pg groups to form a compound of the Formula I wherein $R^1$ and $R^5$ are as defined above:

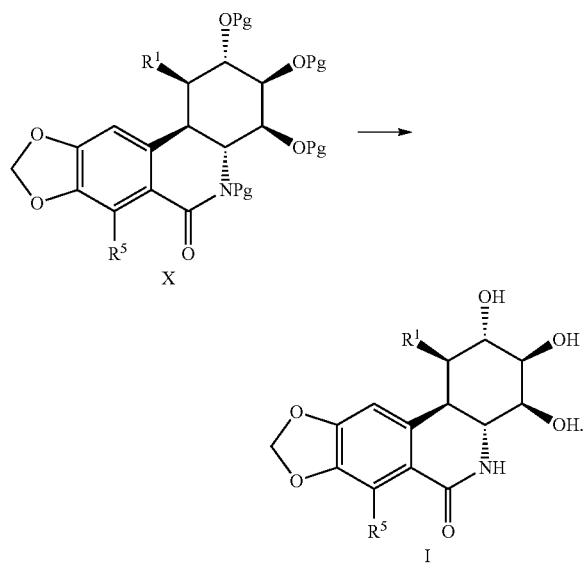

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The application will now be described in greater detail with reference to the drawings in which.

DETAILED DESCRIPTION (I) Definitions

Figure 1:
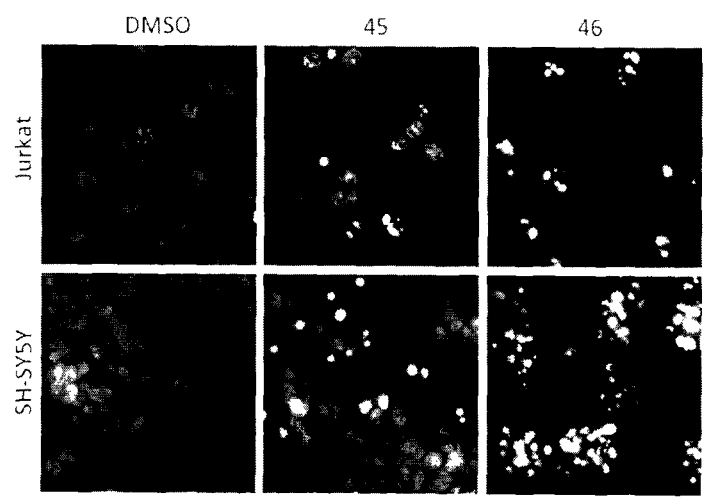
FIG. 1 shows cells stained with Hoechst cell permeable dye and Annexin-V which were used to observe nuclear morphology after exposure to compound I(d) or I(c). Cells with brightly stained, condensed nuclei are considered to be apoptotic (a). Apoptosis was confirmed by Annexin-V binding after 48 hr exposure to either I(d) or I(c) at 0.5 µM concentration (b).
Figure 1:
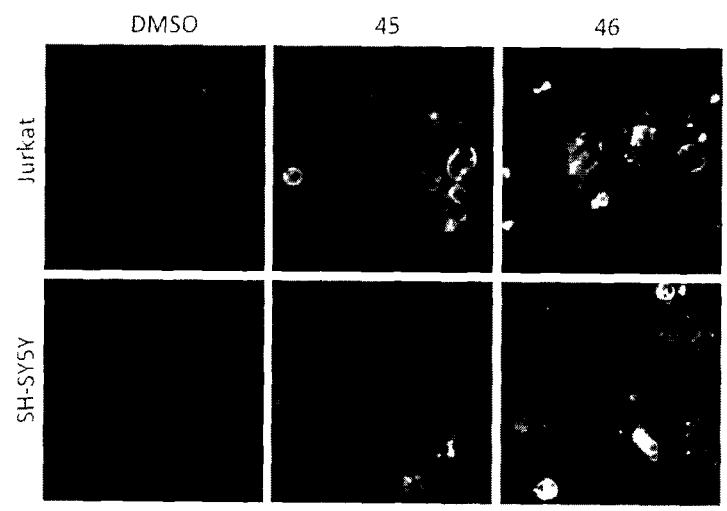

The term "alkyl" as used herein, whether it is used alone or as part of another group, means straight or branched chain, saturated alkyl groups. Generally an "alkyl group" contains 1, 2, 3, 4, 5, or 6 carbon atoms and includes methyl, ethyl, propyl, isopropyl, n-butyl, s-butyl, isobutyl, t-butyl, 2,2-dimethylbutyl, n-pentyl, 2-methylpentyl, 3-methylpentyl, 4-methylpentyl, n-hexyl and the like. It is an embodiment of the application that the alkyl groups are optionally substituted. It is a further embodiment that, in the alkyl groups, one or more, including all, of the hydrogen atoms are optionally replaced with F or $^2H$ and thus includes, for example, trifluoromethyl, pentafluoroethyl and the like.

The term "alkenyl" as used herein means straight and/or branched chain, unsaturated alkyl groups containing from two to six carbon atoms and one to three double bonds, and includes vinyl, allyl, 2-methylprop-1-enyl, but-1-enyl, but-2-enyl, but-3-enyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like. It is an embodiment of the application that the alkenyl groups are optionally substituted. It is a further embodiment that, in the alkenyl groups, one or more, including all, of the hydrogen atoms are optionally replaced with F or $^2H$.

The term "cycloalkyl" as used herein a saturated carbocyclic group generally containing from three to 10 carbon atoms and one or more rings and includes cyclopropyl, cyclobutyl, cyclopentyl, cyclodecyl, bicyclo[2.2.2]octane, bicyclo[3.1.1]heptane, octahydro-1H-indene and the like. It is an embodiment of the application that the cycloalkyl groups are optionally substituted. It is a further embodiment that, in the cycloalkyl groups, one or more, including all, of the hydrogen atoms are optionally replaced with F or $^2H$.

The term "aryl" as used herein refers to cyclic groups that contain at least one aromatic ring. The cyclic groups are either monocyclic, bicyclic or tricyclic, and, when more than one ring is present, the rings are joined in fused, Spiro and/or bridged arrangements. In an embodiment of the application, the aryl group contains from 6 to 14 atoms. It is an embodiment of the application that the aryl groups are optionally substituted. It is a further embodiment that, in the aryl groups, one or more, including all, of the hydrogen atoms are optionally replaced with F or $^2H$ and thus includes, for example, pentafluorophenyl and the like.

The term "halo" as used herein refers to a halogen atom and includes F, Cl, Br and I.

In some cases the chemistries outlined herein may have to be modified, for instance by use of protecting groups, to prevent side reactions of reactive groups attached as substituents. This may be achieved by means of conventional protecting groups.

The terms "protective group" or "protecting group" or "PG" or the like as used herein refer to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, $3^{rd}$ Edition, 1999 and in Kocienski, P. Protecting Groups, 3rd Edition, 2003, Georg Thieme Verlag (The Americas). Examples of suitable protecting groups include but are not limited to t-BOC, Ts, Ms, TBDMS (or TBS), TBDPS, Tf, Bn, allyl, Fmoc, $C_{1-16}$acyl and the like. In certain embodiments, the protecting group is a cyclic protecting group formed by linking two adjacent functional groups, for example, adjacent hydroxyl groups. An example of a cyclic protecting group is a cyclic acetal or ketal, such as dimethyl acetal.

The term "optionally substituted" as used herein means that the referenced group is unsubstituted or substituted with one or more groups that are compatible with the reaction conditions utilized herein and do not impede, but may actually promote, the reaction processes. In an embodiment, the optional substituents are one or more, one to five, one to four, one to three, one to two or one of those substituent groups that are specified for a particular group.

The term "leaving group" as used herein refers to a group that is readily displaceable by a nucleophile, for example, under nucleophilic substitution reaction conditions. Examples of suitable leaving groups include, halo, Ms, Ts, Ns, Tf, Bn, $C_{1-6}$acyl, $C_{1-16}$alkyl, alkylsulphonyl and the like.

The term "isotopic label" as used herein refers an isotopic form of an atom that is other than the most abundant form of that atom in nature. For example isotopic labels of $^{12}C$ atoms include $^{14}C$ and/or $^{13}C$ atom, isotopic labels of $^{1}H$ atoms include $^{2}H$ (deuterium) and/or $^{3}H$ (tritium) atom, and an isotopic label of $^{14}N$ atoms is $^{15}N$. In some cases, the isotope is a radioisotope. In an embodiment of the application, an isotopic labeled compound is prepared using standard methods known in the art. For example, deuterium or tritium are incorporated into a compound using standard techniques, for example by hydrogenation of a suitable precursor using deuterium or tritium gas and a catalyst. Alternatively, a compound containing radioactive iodo is prepared from the corresponding trialkyltin (suitably trimethyltin) derivative using standard iodination conditions, such as [$^{125}I$] sodium iodide in the presence of chloramine-T in a suitable solvent, such as dimethylformamide. In a further embodiment, the trialkyltin compound is prepared from the corresponding non-radioactive halo, suitably iodo, compound using standard palladium-catalyzed stannylation conditions, for example hexamethylditin in the presence of tetrakis(triphenylphosphine) palladium (0) in an inert solvent, such as dioxane, and at elevated temperatures, suitably 50-100° C.

The term "suitable", as in for example, "suitable protecting group", "suitable leaving group" or "suitable reaction conditions" means that the selection of the particular group or conditions would depend on the specific synthetic manipulation to be performed, and the identity of the molecule to be transformed, but the selection would be well within the skill of a person trained in the art. All process steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

t-BOC as used herein refers to the group t-butyloxycarbonyl.
Ac as used herein refers to the group acetyl.
Ts (tosyl) as used herein refers to the group p-toluenesulfonyl
Ms as used herein refers to the group methanesulfonyl
TBDMS (TBS) as used herein refers to the group t-butyldimethylsilyl.
TBDPS as used herein refers to the group t-butyldiphenylsilyl.
Tf as used herein refers to the group trifluoromethanesulfonyl.
Ns as used herein refers to the group naphthalene sulphonyl.
Bn as used herein refers to the group benzyl.
Fmoc as used here refers to the group fluorenylmethoxycarbonyl.

In all of the compounds disclosed herein, that is compounds of the Formulae I-X, one or more, including all, of the hydrogen atoms may be replaced with F. A person skilled in the art would appreciate that only those hydrogens available for substitution by fluorine would be replaceable by fluorine.

The term "compound(s) of the application" or "intermediate compounds" used herein means compound(s) of Formulae I or II as defined above, or any other novel compounds or intermediates defined above, stereoisomers thereof or pharmaceutically acceptable salts, solvates or prodrugs thereof.

The compounds of the application all have at least one asymmetric centre. Where the compounds according to the application possess more than one asymmetric centre, they may exist as diastereomers. It is to be understood that all such isomers and mixtures thereof in any proportion are encompassed within the scope of the present application. It is to be understood that while the stereochemistry of the compounds of the application may be as provided for in any given compound listed herein, such compounds of the application may also contain certain amounts (e.g. less than 20%, preferably less than 10%, more preferably less than 5%) of compounds of the application having alternate stereochemistry.

The term "pharmaceutically acceptable" means compatible with the treatment of animals, in particular, humans.

The term "pharmaceutically acceptable salt" means an acid addition salt or base addition salt, which is suitable for or compatible with the treatment of patients.

The term "pharmaceutically acceptable acid addition salt" as used herein means any non-toxic organic or inorganic salt of any base compound of the application, or any of its intermediates. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of the compounds of the application are more soluble in water and various hydrophilic organic solvents, and generally demonstrate higher melting points in comparison to their free base forms. The selection of the appropriate salt will be known to one skilled in the art. Other non-pharmaceutically acceptable salts, e.g. oxalates, may be used, for example, in the isolation of the compounds of the application, for laboratory use, or for subsequent conversion to a pharmaceutically acceptable acid addition salt. In embodiments of the application, the pharmaceutically acceptable acid addition salt is the hydrochloride salt, or the $H_3PO_4$ salt. The formation of a desired compound salt is achieved using standard techniques. For example, the neutral compound is treated with an acid or base in a suitable solvent and the formed salt is isolated by filtration, extraction or any other suitable method.

The term "pharmaceutically acceptable basic addition salt" as used herein means any non-toxic organic or inorganic base addition salt of any acid compound of the application, or any of its intermediates. Illustrative inorganic bases which form suitable salts include lithium, sodium, potassium, calcium, magnesium or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmaceutically acceptable basic addition salts, may be used, for example, in the isolation of the compounds of the application, for laboratory use, or for subsequent conversion to a pharmaceutically acceptable acid addition salt.

The term "solvate" as used herein means a compound of the application or a pharmaceutically acceptable salt of a compound of the application, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions.

Compounds of the application include prodrugs. In general, such prodrugs will be functional derivatives of a compound of the application, which are readily convertible in vivo into the compound from which it is notionally derived. Prodrugs of the compounds of the application may be conventional esters formed with available hydroxy, or amino groups. For example, an available OH or nitrogen in a compound of the application may be acylated using an activated acid in the presence of a base, and optionally, in inert solvent (e.g. an acid chloride in pyridine). Some common esters which have been utilized as prodrugs are phenyl esters, aliphatic ($C_8$-$C_{24}$) esters, acyloxymethyl esters, carbamates and amino acid esters. In certain instances, the prodrugs of the compounds of the application are those in which one or more of the hydroxy groups in the compounds is masked as groups which can be converted to hydroxy groups in vivo. Conventional procedures for the selection and preparation of suitable prodrugs are described, for example, in "Design of Prodrugs" ed. H. Bundgaard, Elsevier, 1985.

The term "subject" as used herein includes all members of the animal kingdom including human. The subject is preferably a human.

The term "cancer" as used herein refers to a class of diseases or disorders characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. Examples of cancer that may be treated using the compounds of the application include but are not limited to, prostate cancer, colon cancer, breast cancer, bladder cancer, lung cancer, ovarian cancer, endometrial cancer renal cancer and pancreatic cancer.

The term a "therapeutically effective amount", "effective amount" or a "sufficient amount" of a compound of the present application is a quantity sufficient to, when administered to the subject, including a mammal, for example a human, effect beneficial or desired results, including clinical results, and, as such, an "effective amount" or synonym thereto depends upon the context in which it is being applied. In the context of disease, therapeutically effective amounts of the compounds of the present application are used to treat, modulate, attenuate, reverse, or affect a disease or conditions for example, cancer in a subject. An "effective amount" is intended to mean that amount of a compound that is sufficient to treat, prevent or inhibit such diseases or conditions. The amount of a given compound of the present application that will correspond to such an amount will vary depending upon various factors, such as the given drug or compound, the pharmaceutical formulation, the route of administration, the type of disease or disorder, the identity of the subject or host being treated, and the like, but can nevertheless be routinely determined by one skilled in the art. Also, as used herein, a "therapeutically effective amount" of a compound of the present application is an amount which prevents, inhibits, suppresses or reduces a disease or conditions for example, cancer as determined by clinical symptoms or the amount of cancer cells, in a subject as compared to a control. As defined herein, a therapeutically effective amount of a compound of the present application may be readily determined by one of ordinary skill by routine methods known in the art.

In an embodiment, a therapeutically effective amount of a compound of the present application ranges from about 0.1 to about 100 mg/kg body weight, suitably about 2 to about 50 mg/kg body weight. The skilled artisan will appreciate that certain factors may influence the dosage required to effectively treat a subject, or prevent a subject, suffering from a disease or condition for example cancer, and these factors include, but are not limited to, the severity of the disease or disorder, previous treatments, the general health and/or age of the subject and other diseases present.

As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

Moreover, a "treatment" or "prevention" regime of a subject with a therapeutically effective amount of the compound of the present application may consist of a single administration, or alternatively comprise a series of applications. For example, the compound of the present application may be administered at least once a week. However, in another embodiment, the compound may be administered to the subject from about one time per week to about once daily for a given treatment. In yet another embodiment the compound may be administered more than once daily up to 5 times per day. The length of the treatment period depends on a variety of factors, such as the severity of the disease, the age of the patient, the concentration and the activity of the compounds of the present application, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

As used herein, "administered contemporaneously" means that two substances are administered to a subject such that they are both biologically active in the subject at the same time. The exact details of the administration will depend on the pharmacokinetics of the two substances in the presence of each other, and can include administering one substance within 24 hours of administration of the other, if the pharmacokinetics are suitable. Designs of suitable dosing regimens are routine for one skilled in the art. In particular embodiments, two substances will be administered substantially simultaneously, i.e. within minutes of each other, or in a single composition that comprises both substances.

"Palliating" a disease or disorder means that the extent and/or undesirable clinical manifestations of a disorder or a disease state are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with cancer or manifesting a symptom associated with cancer.

To "inhibit" or "suppress" or "reduce" a function or activity, is to reduce the function or activity when compared to otherwise same conditions except for a condition or parameter of interest, or alternatively, as compared to another condition. The terms "inhibitor" and "inhibition", in the context of the present application, are intended to have a broad meaning and encompass compounds of the application which directly or indirectly (e.g., via reactive intermediates, metabolites and the like) act on cancer.

The term "a cell" as used herein includes a plurality of cells. Administering a compound to a cell includes in vivo, ex vivo and in vitro treatment.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The definitions and embodiments described in particular sections are intended to be applicable to other embodiments herein described for which they are suitable as would be understood by a person skilled in the art.

(II) Compounds

The present application includes compounds Formula I:

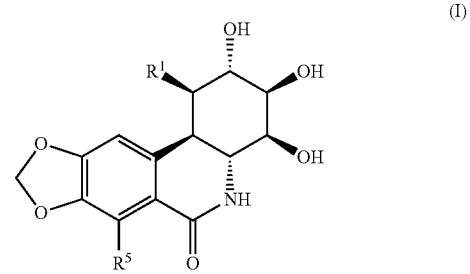

(I)

wherein:

$R^1$ is selected from $C(O)R^2$, $C(O)NR^2R^3$, $CH=NR^2$, $CH_2NR^2R^3$, $CH_2OR^2$, $CH_2R^2$, $CH=CR^2R^3$, $NR^2R^3$, $NHC(O)R^2$, $NHC(O)OR^2$, $NHC(O)NR^2R^3$, $CH_2OC(O)NR^2R^3$, $CH_2NHC(O)R^2$, $CH_2NHC(O)OR^2$, $CH_2CHC(O)NR^2R^3$, $CH_2OC(O)R^2$ and $C(O)OR^4$; and $R^2$ and $R^3$ are independently selected from H, $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro;

$R^4$ is selected from $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro; and $R^5$ is selected from H and OH; and in each alkyl, alkenyl, cycloalkyl and aryl, one or more available H are optionally replaced with F, or a pharmaceutically acceptable salt, solvate or prodrug thereof.

In an embodiment of the application $R^1$ is selected from C(O)Me, C(O)H, CH=NH and $CH_2NH_2$, $CH_2OH$ and $CH_2OC(O)CH_3$. In an embodiment of the application $R^1$ is selected from $CH_2OH$ and $CH_2OC(O)CH_3$. In another embodiment of the application $R^5$ is H.

In another embodiment, the compounds of Formula I comprise an isotopic label. Therefore the present application also includes compounds of Formula I wherein one or more atoms are replaced with an isotopic label. In an embodiment the isotopic label is $^2H$, $^3H$, $^{13}C$, $^{15}N$, $^{123}I$ and $^{18}F$.

(III) Compositions and Uses/Methods

As hereinbefore mentioned, novel compounds of the Formula I, and intermediates of the Formula II have been prepared. Accordingly, the present application includes all uses of the compounds of Formula I and the intermediates of Formula II including their use in therapeutic methods and compositions for treatment of cancer, their use in diagnostic assays and their use as research tools.

In particular, the present application includes the use of one or more compounds of Formula I, and/or pharmaceutically acceptable salts, solvates and prodrugs thereof, as a medicament, the compound of Formula I being:

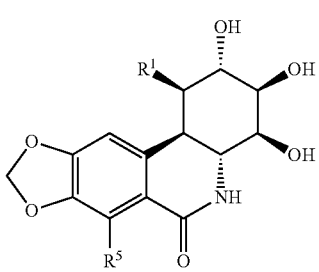

(I)

wherein:

$R^1$ is selected from $C(O)R^2$, $C(O)NR^2R^3$, $CH=NR^2$, $CH_2NR^2R^3$, $CH_2OR^2$, $CH_2R^2$, $CH=CR^2R^3$, $NR^2R^3$, $NHC(O)R^2$, $NHC(O)OR^2$, $NHC(O)NR^2R^3$, $CH_2OC(O)NR^2R^3$, $CH_2NHC(O)R^2$, $CH_2NHC(O)OR^2$, $CH_2CHC(O)NR^2R^3$, $CH_2OC(O)R^2$ and $C(O)OR^4$; and $R^2$ and $R^3$ are independently selected from H, $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro;

$R^4$ is selected from $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro; and $R^5$ is selected from H and OH; and in each alkyl, alkenyl, cycloalkyl and aryl, one or more available H are optionally replaced with F.

In an aspect of the application there is also included a use of one or more compounds of Formula I as defined above, and/or pharmaceutically acceptable salts, solvates and/or prodrugs thereof, to treat cancer.

In a further aspect of the application there is included a method of treating cancer comprising administering an effective amount of one or more compounds of Formula I as defined above, and/or pharmaceutically acceptable salts, solvates and/or prodrugs thereof, to a subject in need thereof.

In another aspect of the present application there is included a use of one or more compounds of Formula I, as defined above, and/or pharmaceutically acceptable salts, solvates and/or prodrugs thereof, as a medicament.

In another aspect of the application there is included a composition comprising a mixture of two or more compounds, said compounds being selected from a compound of Formula I as defined above, and a pharmaceutically acceptable salt, solvate and prodrug thereof.

The compounds of the application are suitably formulated into pharmaceutical compositions for administration to human subjects in a biologically compatible form suitable for administration in vivo. Accordingly, the present application further includes a pharmaceutical composition comprising one or more compounds of Formula I, as defined above, and/or pharmaceutically acceptable salts, solvates and/or prodrugs thereof, and a pharmaceutically acceptable carrier and/or diluent.

The pharmaceutical compositions containing the compounds of the application can be prepared by known methods for the preparation of pharmaceutically acceptable compositions, which can be administered to subjects, such that an effective quantity of the active substance is combined in a mixture with a pharmaceutically acceptable vehicle. Suitable vehicles are described, for example, in Remington's Pharmaceutical Sciences (2000-20th edition) and in The United States Pharmacopeia: The National Formulary (USP 24 NF19) published in 1999). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The compounds of the application are used in the form of the free base, in the form of prodrugs, salts and/or solvates. All forms, including mixtures thereof, are within the scope of the application.

In accordance with embodiments of the methods of the application, the described compounds of Formula I, salts, solvates and/or prodrugs thereof are administered to a patient in a variety of forms depending on the selected route of administration, as will be understood by those skilled in the art. For example, the compounds of the application are administered by oral, parenteral, buccal, sublingual, nasal, rectal, patch, pump or transdermal (topical) administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time.

In an embodiment of the application, the compounds of the application are orally administered, for example, with an inert diluent or with an assimilable edible carrier, or they are enclosed in hard or soft shell gelatin capsules, or they are compressed into tablets, or they are incorporated directly with the food of a diet. In an embodiment, for oral therapeutic administration, the compounds are incorporated with excipient and used in the form of ingestible tablets, buccal tablets, troches, capsules, elixirs, suspensions, syrups, wafers, and the like.

In a further embodiment, the compounds of the application are administered parenterally. For example, solutions of a compound are prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. As noted above, person skilled in the art would know how to prepare suitable formulations.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. Ampoules are convenient unit dosages.

In a further embodiment, compositions for nasal administration are conveniently formulated as aerosols, drops, gels and powders. Aerosol formulations typically comprise a solution or fine suspension of a compound in a physiologically acceptable aqueous or non-aqueous solvent and are usually presented in single or multidose quantities in sterile form in a sealed container, which can take the form of a cartridge or refill for use with an atomizing device. Alternatively, the sealed container is a unitary dispensing device such as a single dose nasal inhaler or an aerosol dispenser fitted with a metering valve, which is intended for disposal after use. Where the dosage form comprises an aerosol dispenser, it will contain a propellant, which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges and pastilles, wherein the compound is formulated with a carrier such as sugar, acacia, tragacanth, or gelatin and glycerine. Compositions for rectal administration are conveniently in the form of suppositories containing a conventional suppository base such as cocoa butter.

Compositions for topical administration include, for example, propylene glycol, isopropyl alcohol, mineral oil and glycerin. Preparations suitable for topical administration include liquid or semi-liquid preparations such as liniments, lotions, applicants, oil-in-water or water-in-oil emulsions such as creams, ointments or pastes; or solutions or suspensions such as drops. In addition to the aforementioned ingredients, the topical preparations may include one or more additional ingredients such as diluents, buffers, flavouring agents, binders, surface active agents, thickeners, lubricants, preservatives, e.g. methyl hydroxybenzoate (including antioxidants), emulsifying agents and the like.

Sustained or direct release compositions can be formulated, e.g. liposomes or those wherein the active compound is protected with differentially degradable coatings, such as by microencapsulation, multiple coatings, etc. It is also possible to freeze-dry the compounds and use the lypolizates obtained, for example, for the preparation of products for injection.

The dosage administered will vary depending on the use and known factors such as the pharmacodynamic characteristics of the particular substance, and its mode and route of administration; age, health, and weight of the individual recipient; nature and extent of symptoms; kind of concurrent treatment; frequency of treatment; and the effect desired.

(IV) Processes

The present application also includes a process for preparing a compound of Formula II

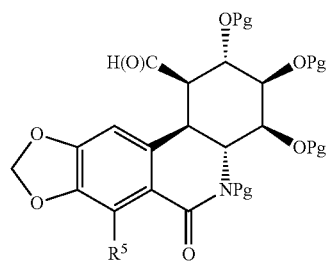

(II)

wherein $R^5$ is selected from H and OPg and each Pg may be the same or different and represent suitable protecting groups or any two adjacent Pg are joined to form a suitable cyclic protecting group;
the process comprising:
(i) reacting a compound of the Formula III with an aluminum acetylide derived from a compound of the Formula IV, followed by protection to form a compound of the Formula V, wherein $R^5$ and each Pg is as defined above:

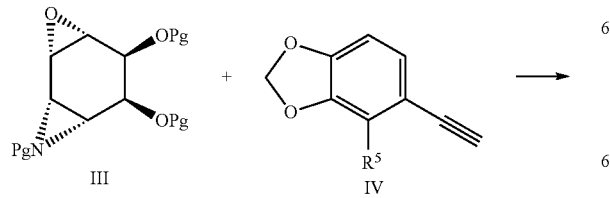

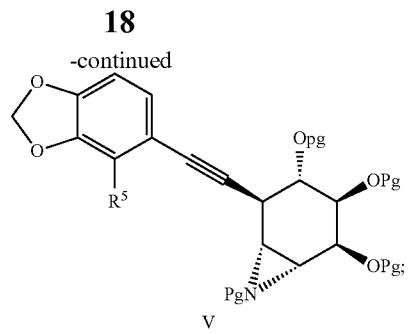

(ii) reducing the compound of Formula V to form a cis-alkene of the Formula VI, wherein $R^5$ and each Pg is as defined above:

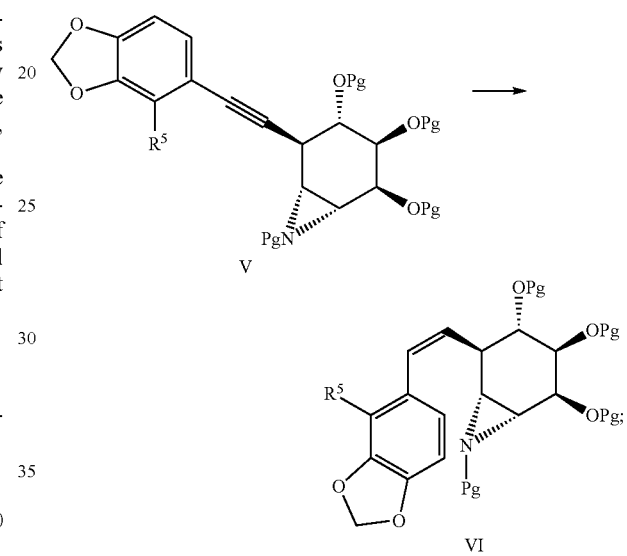

(iii) reacting the compound of the Formula VI under solid-state, silica gel catalysis conditions to form a compound of the Formula VII, wherein $R^5$ and each Pg is as defined above:

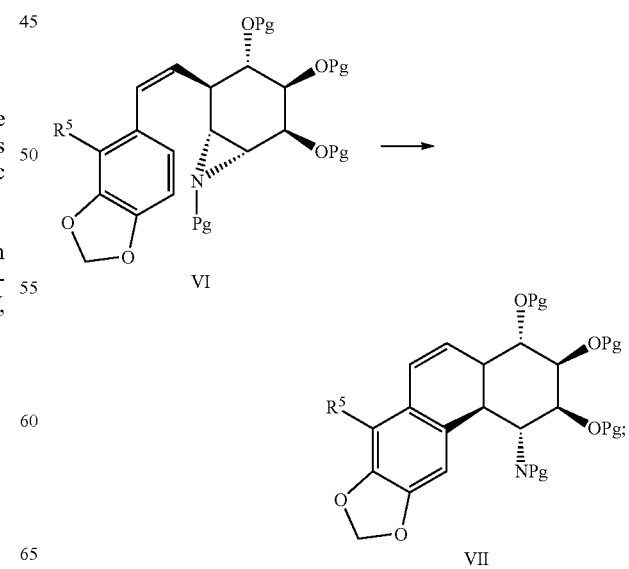

(iv) oxidatively cleaving the non-aromatic double bond in the compound of the Formula VII to form an intermediate diketone of the Formula VIII which cyclizes to form a compound of the Formula IX, wherein $R^5$ and each Pg is as defined above:

and (v) oxidizing the compound of the Formula IX to form a compound of Formula II, wherein $R^5$ and each Pg is as defined above:

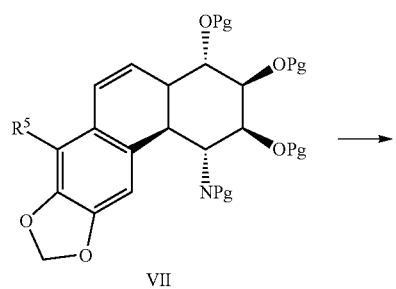

VII

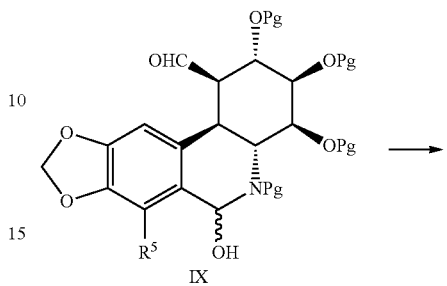

IX

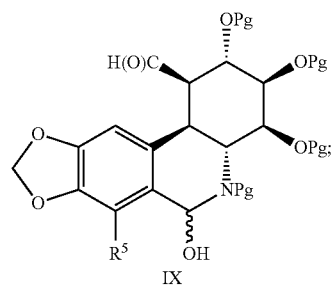

VIII

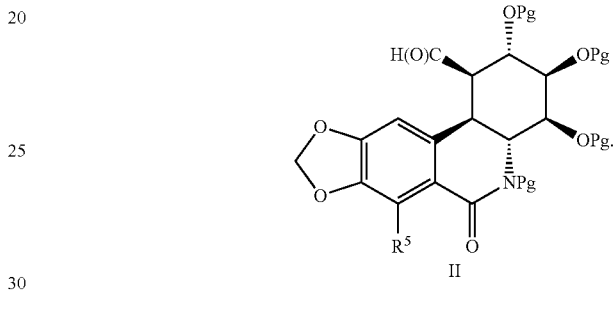

II

IX

In an embodiment of the application, the Pg group on the aziridine nitrogen in the compound of Formula III is Ts. In another embodiment, the Pg groups on the oxygen atoms of the compound of Formula III are linked to form a cyclic acetal group in particular dimethyl acetal. In a further embodiment the protecting group (Pg) added in step (i) to the oxygen following ring opening of the epoxide is t-butyldimethylsilyl (TBDMS).

According to a specific embodiment, the process of the present application is directed to the synthesis of a compound according to Formula II using the reaction conditions shown in Scheme 1.

Scheme 1

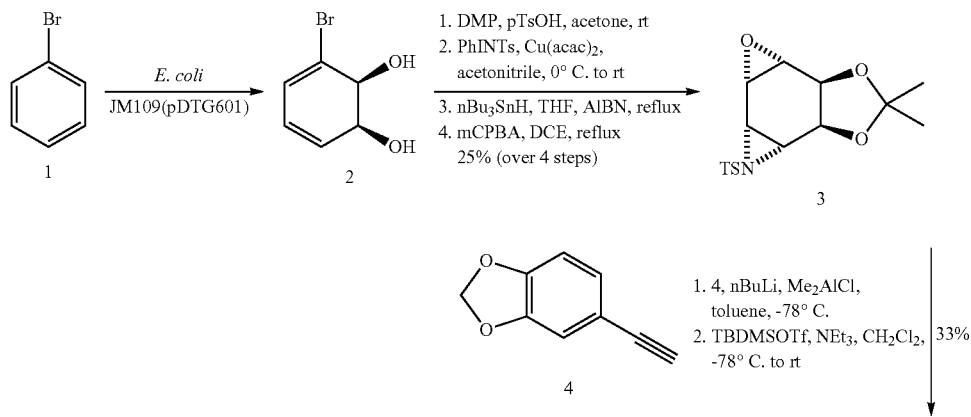

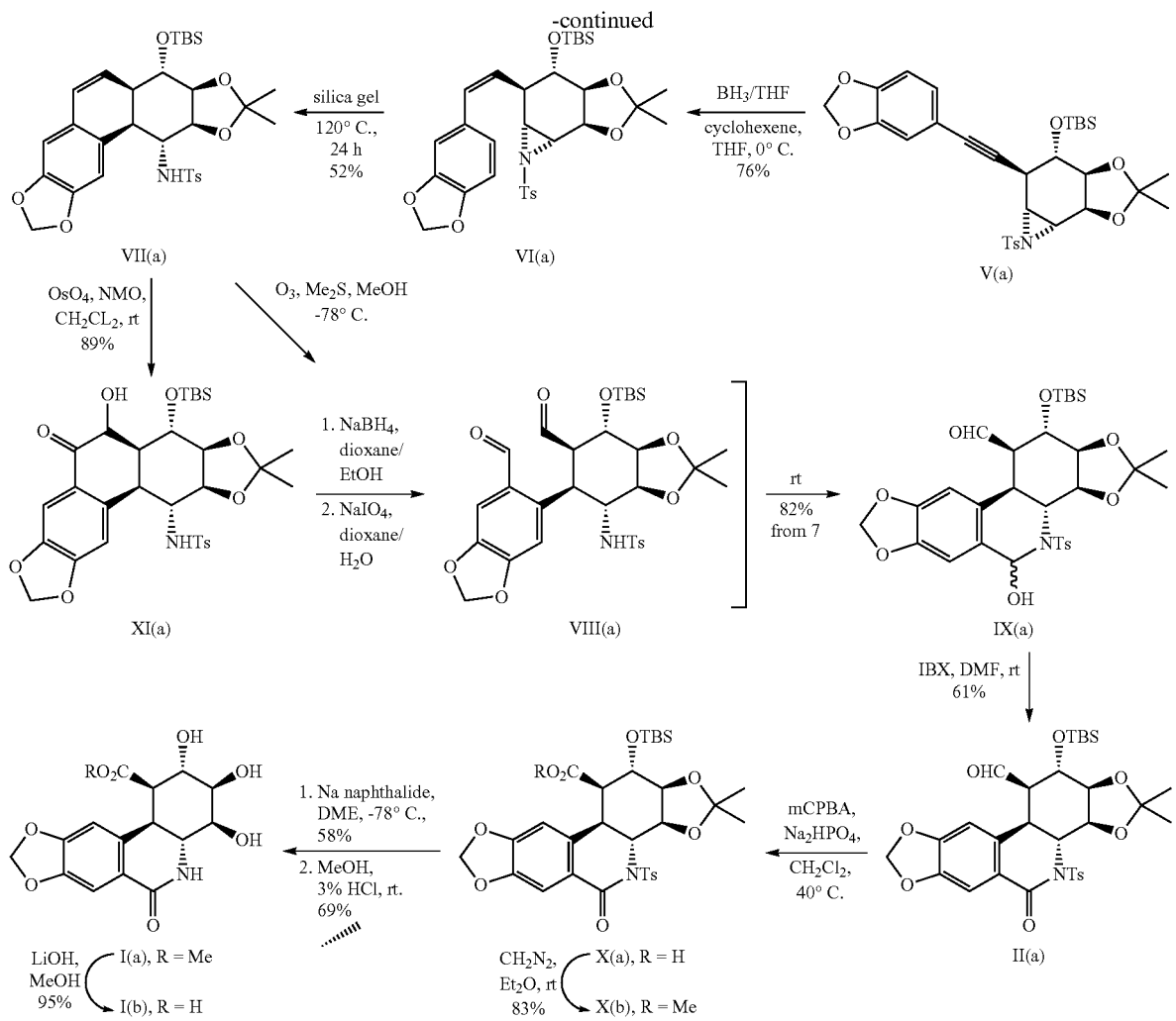

According to this embodiment the aluminum acetylide of the compound of Formula IV described in (i) above is formed by the addition of nBuLi and dimethylaluminum chloride in toluene at reduced temperature, for example about −78° C. Reaction of the compound of Formula III with the aluminum acetylide of the compound of Formula IV is followed by protection of the hydroxyl product of the ring opening. In a particular embodiment the hydroxyl is protected by reaction with TBDMSOTf in the presence of base, for example $Et_3N$.

In another embodiment of the process, in (ii), reduction of the alkyne to the cis alkene is achieved using a hydride reducing agent, such as a borohydride reducing agent, for example $BH_3$, in a suitable solvent at reduced temperature, for example about 0° C. In a further embodiment of the process, in (ii), reduction of the alkyne to the cis alkene is achieved using hydrogenation conditions, for example $H_2$ gas in the presence of a catalyst.

In another embodiment of the process, in (iii), the cis alkene compound of Formula VI is adsorbed onto silica gel and heated without solvent. In a particular embodiment the reaction mixture is heated to 120° C. for approximately 24 hours to provide a compound of Formula VII.

In a further embodiment of the process, in (iv), the compound of Formula VII is converted to the intermediate VIII by ozonolysis under suitable reaction conditions, for example in $Me_2S$ and MeOH at reduced temperature, for example at about −78° C. In another embodiment, in (iv), the intermediate of Formula VIII is formed by a two step process comprising oxidation with osmium tetroxide ($OsO_4$) in the presence of N-methylmorpholine N-oxide (NMO), in $CH_2Cl_2$ to give a keto alcohol intermediate of the Formula XI, followed by reduction, for example with sodium borohydride, then periodate cleavage under suitable conditions to give the intermediate of Formula VIII.

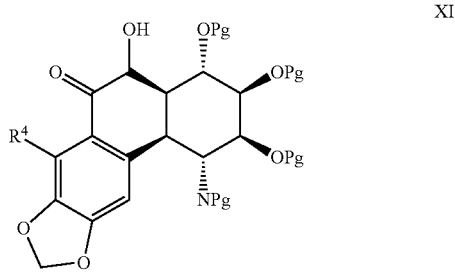

XI

In another embodiment of the process, in (v), oxidation of the compound of Formula IX to the compound of Formula II is carried out using 2-iodoxybenzoic acid (IBX) under suitable conditions.

Compounds of the Formulae III and IV are prepared using methods known in the art (see for example, Schilling et al. Can J. Chem. 79:1659 (2001); Endoma, et al. Org. Process Res. Dev. 6:525 (2002)).

In another aspect of the application there is include a process for preparing a compound of Formula I

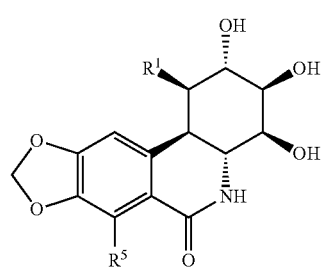

(I)

wherein:

$R^1$ is other than C(O)H and is selected from $C(O)R^2$, $C(O)NR^2R^3$, $CH=NR^2$, $CH_2NR^2R^3$, $CH_2OR^2$, $CH_2R^2$, $CH=CR^2R^3$, $NR^2R^3$, $NHC(O)R^2$, $NHC(O)OR^2$, $NHC(O)NR^2R^3$, $CH_2OC(O)NR^2R^3$, $CH_2NHC(O)R^2$, $CH_2NHC(O)OR^2$, $CH_2CHC(O)NR^2R^3$, $CH_2OC(O)R^2$ and $C(O)OR^4$; and $R^2$ and $R^3$ are independently selected from H, $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro;

$R^4$ is selected from $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro; and $R^5$ is selected from H and OH; and in each alkyl, alkenyl, cycloalkyl and aryl, one or more available H are optionally replaced with F, comprising:

(i) reacting a compound of the Formula II, wherein $R^5$ is selected from H and OPg and each Pg may be the same or different and represent suitable protecting groups or any two adjacent Pg are joined to form a suitable cyclic protecting group, under conditions to convert the aldehyde moiety in one or more steps to a group, other than C(O)H, selected from $C(O)R^2$, $C(O)NR^2R^3$, $CH=NR^2$, $CH_2NR^2R^3$, $CH_2OR^2$, $CH_2R^2$, $CH=CR^2R^3$, $NR^2R^3$, $NHC(O)R^2$, $NHC(O)OR^2$, $NHC(O)NR^2R^3$, $CH_2OC(O)NR^2R^3$, $CH_2NHC(O)R^2$, $CH_2NHC(O)OR^2$, $CH_2CHC(O)NR^2R^3$, $CH_2OC(O)R^2$ and $C(O)OR^4$, wherein $R^2$, $R^3$ and $R^4$ are as defined above, to form a compound of the Formula X wherein $R^1$, $R^5$ and each Pg are as defined above:

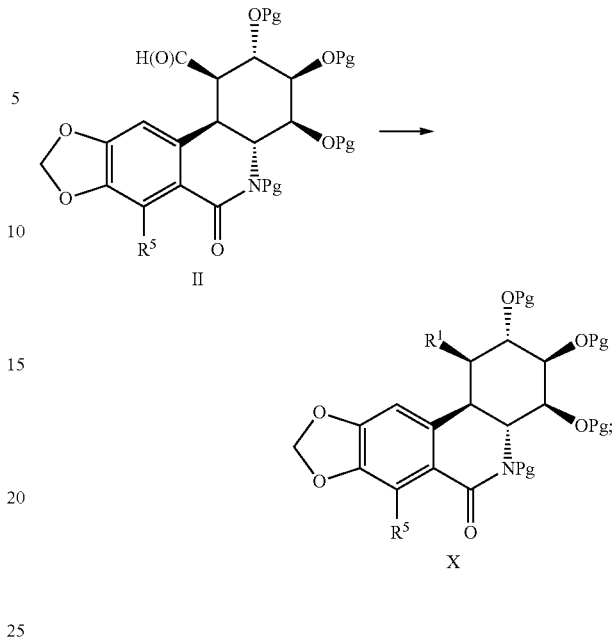

(ii) removing the Pg groups to form a compound of the Formula I wherein $R^1$ and $R^5$ are as defined above:

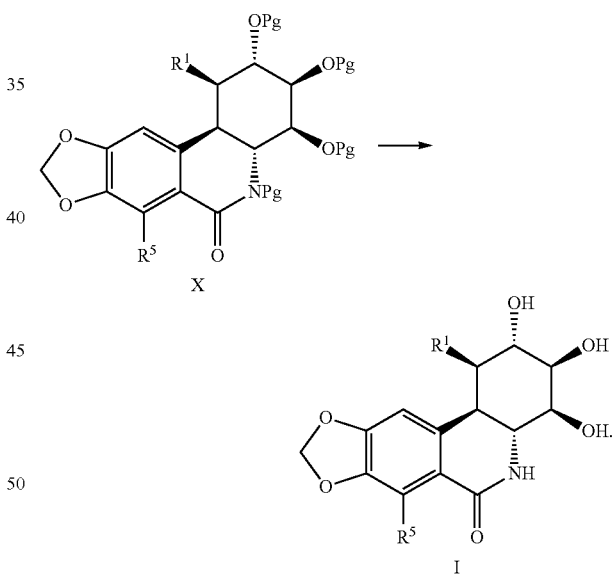

In another aspect of the application there is provided a process for preparing a compound of Formula I wherein $R^1$ is $C(O)OR^4$, wherein in (i) above the conditions comprise oxidizing the compound of the Formula II to the corresponding carboxylic acid followed by alkylation with a compound of the Formula $R^4$-LG, wherein LG is a suitable leaving group, to form, after removal of the Pg groups in (ii), the compound of the Formula I.

In another aspect of the application there is provided a process for preparing a compound of Formula I wherein $R^1$ is $CH=NR^2$ wherein in (i) above the conditions comprise reacting the compound of the Formula II with an amine of the Formula $R^2-NH_2$ to form, after removal of the Pg groups in (ii), the compound of the Formula I.

In another aspect of the application there is provided a process for preparing a compound of Formula I wherein $R^1$ is $CH_2NR^2R^3$ wherein in step (i) above the conditions comprise reacting the compound of the Formula II with an amine, followed by reduction and optional alkylation with a compound of the Formula $R^3$-LG, wherein LG is a suitable leaving group, to form, after removal of the Pg groups in (ii), the compound of the Formula I.

In another aspect of the application there is provided a process for preparing a compound of Formula I wherein $R^1$ is $CH=CR^2R^3$ wherein in step (i) above the conditions comprise reacting the compound of the Formula II with a phosphonium ylide of the formula $R^2R^3CH=PPh_3$ under Wittig reaction conditions to form, after removal of the Pg groups in (ii), the compound of Formula I.

In another aspect of the application there is provided a process for preparing a compound of Formula I wherein $R^1$ is $C(O)NR^2R^3$, wherein in (i) above the conditions comprise oxidizing the compound of Formula II to the corresponding carboxylic acid followed by reaction with an amine of the formula $H_2NR^2R^3$ under amide bond forming conditions to form, after removal of the Pg groups in (ii), the compound of the Formula I.

In another aspect of the application there is provided a process for preparing a compound of Formula I wherein $R^1$ is $NR^2R^3$, wherein in (i) above the conditions comprise oxidizing the compound of Formula II to the corresponding carboxylic acid followed by subjecting the C(O)OH group to Curtius rearrangement to form a compound of Formula X, wherein $R^1$ is $NH_2$. This amine can be alkylated with various $R^2$ and/or $R^3$ groups. Alternatively, the C(O)OH groups can be converted to an amide ($CONH_2$) and the amide subjected to Hoffman degradation to produce, after hydrolysis C-1 amine. These methods are known to those skilled in the art.

Also included in the present application is a process for preparing a compound of Formula I

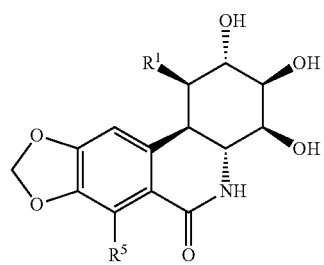

(I)

wherein $R^1$ is C(O)H and $R^5$ is H or OH, comprising removing the Pg groups from a compound of Formula II as defined above to form the compound of the Formula I.

(V) Examples

The following non-limiting examples are illustrative of the present application: Examples 1-10 refer to compounds as shown in Scheme 1.

Example 1

Preparation of (1S,2R,3R,4R,5S,6R)-3,4-(Isopropylidenedioxy)-5-[(tert-butyldimethylsilyl)oxy]-6-2-Benzo[1.3]dioxol-5-ylethynyl-(4'-methylphenylsulfonyl)-7-azabicyclo[4.1.0]heptane V(a)

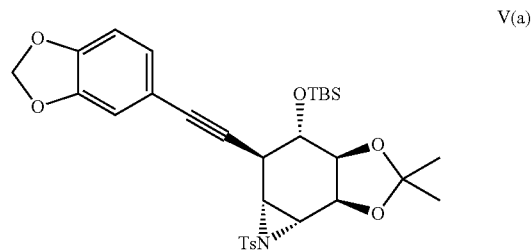

V(a)

To a solution of acetylene 4 (2.74 g, 18.75 mmol) in 18 mL dry toluene was added at −78° C. 8.33 mL of a solution of nBuLi in hexanes (2.25 M, 18.75 mmol). The solution was stirred for 10 minutes before 18.75 mL of a solution of $Me_2AlCl$ (1.0M in $CH_2Cl_2$, 18.75 mmol) was added dropwise. The reaction flask was allowed to warm to room temperature and stir for 1 h. The reaction flask was then cooled to −20° C. and 18 mL of a solution of epoxide 3 (3.16 g, 9.38 mmol) in toluene was added dropwise over 20 min. The reaction was stirred at −20° C. for 3.5 h before being place in an ice bath and allowed to slowly warm to room temperature and stir for 12 h. The reaction was cooled in an ice bath and quenched with 1 M HCl. Ethyl acetate (200 mL) was added and the layers where separated. The aqueous phase was extracted 3×100 mL EtOAc and the combined organic layers dried over $Na_2SO_4$. Concentration under reduced pressure and purification by flash column chromatography (hexanes:ethyl acetate, 7:1 to 4:1) afforded alcohol intermediate which was immediately subjected to protection protocol (2.01 g, 44%); $[\alpha]^{22}_D$ −113.05 (c 0.5, $CHCl_3$); $R_f$ 0.30 (hexanes:ethyl acetate 2:1); IR (film) v 3491, 2988, 1163 cm$^{-1}$; $^1$H NMR (300 MHz, $CDCl_3$) δ: 7.78 (d, J=8.1 Hz, 2H), 7.38 (d, J=8.1 Hz, 2H), 6.91 (dd, J=8.2 Hz, 1.8 Hz 1H), 6.83 (d, J=1.5 Hz, 1H), 6.73 (d, J=7.9 Hz, 1H), 5.97 (s, 2H), 4.47 (d, J=6.4 Hz, 1H), 4.22 (dd, J=6.1, 4.4 Hz, 1H), 3.98 (m, 1H), 3.40 (d, J=6.4 Hz, 1H), 3.24 (m, 2H), 3.06 (d, J=9.6 Hz, 1H), 2.47 (s, 3H), 1.49 (s, 3H), 1.32 (s, 3H) ppm; $^{13}$C NMR (75 MHz, $CDCl_3$) δ: 148.1, 147.5, 145.7, 134.2, 130.4, 128.1, 126.4, 116.2, 111.8, 110.3, 108.6, 101.5, 84.2, 83.8, 75.4, 70.1, 68.7, 42.3, 40.5, 31.1, 27.4, 25.2, 21.9 ppm; HRMS (FAB M$^+$) calcd for $C_{25}H_{25}NO_7S$ 484.1430. found 484.1428.

Alcohol intermediate (240 mg, 0.49 mmol) was dissolved in 5 mL of $CH_2Cl_2$ and triethylamine (0.14 mL, 1.04 mmol) was added. The reaction flask was cooled to −78° C. and t-butyldimethylsilytriflate (0.12 mL, 0.546 mmol) was added dropwise to the stirring solution. After stirring for 30 minutes at −78° C. the reaction was quenched with water and the two phases separated. The aqueous phase was extracted with $CH_2Cl_2$ (2×15 mL) and the combined organic solution was washed sequentially with 5% citric acid (2 mL) and brine (2 mL) before drying over sodium sulfate. The solvent was removed under reduced pressure and the residue was purified by flash column chromatography (hexane:ethyl acetate, 9:1 to 2:1) affording V(a) (0.276 g, 93%) as a colorless oil; $[\alpha]^{24}_D$ +57.7 (c 0.5, CHCl$_3$); R$_f$ 0.49 (hexanes:ethyl acetate, 2:1); IR (film) v 2953, 2929, 2892, 2856, 1599, 1490 cm$^{-1}$; $^1$H NMR (300 MHz, CDCl$_3$) δ: 7.83 (d, J=8.1 Hz, 2H), 7.38 (d, J=8.1 Hz, 2H), 6.94 (d, J=8.1 Hz, 1H), 6.84 (s, 1H), 6.77 (d, J=8.1 Hz, 1H), 5.99 (s, 2H), 4.45 (d, J=5.1 Hz, 2H), 3.83 (m, 2H), 3.26 (m, 2H), 2.84 (d, J=7.5 Hz), 2.47 (s, 3H), 1.52 (s, 3H), 1.35 (s, 3H), 0.87 (s, 9H), 0.11 (s, 6H) ppm; $^{13}$C NMR (75 MHz, CDCl$_3$) δ: 147.8, 147.3, 134.7, 129.8, 127.9, 126.1, 111.6, 109.7, 108.4, 101.3, 86.3, 83.5, 71.7, 43.2, 39.53, 34.58, 27.9, 25.8, 25.79, 25.7, 21.7, 18.12, −4.4, −4.7 ppm; HRMS-EI Calcd for C$_{30}$H$_{36}$NO$_7$SSi: 540.1481. Found, 540.1487; Anal. calcd for C$_{31}$H$_{39}$NO$_7$SSi C, 62.28; H, 6.58. found C, 62.22; H, 6.73.

Example 2

1S,2R,3R,4R,5S,6R)-3,4-(Isopropylidenedioxy)-5-[(tert-butyldimethylsilyl)oxy]-6-2-Benzo[1,3]dioxol-5-ylethenyl-(4'-methylphenylsulfonyl)-7-azabicyclo[4.1.0]heptane VI(a)

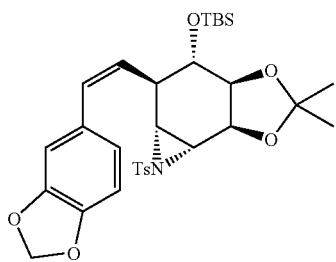

To a 1.0 M solution of BH$_3$.THF complex (2.5 mL, 2.5 mmol) was added cyclohexene (0.484 mL, 4.77 mmol) at 0° C. After 10 minutes a heavy precipitate was formed. The reaction mixture was kept at 0° C. for 1 h before acetylene derivative V(a) (0.356 mg, 0.596 mmol) in 4.5 mL of THF was added. The reaction mixture was stirred at 0° C. until total consumption of starting material (2 h, TLC) before being quenched with 1 mL HOAc. 60 mL EtOAc were added and the reaction mixture was washed with saturated aq. NaHCO$_3$ (2×15 mL), H$_2$O (2×15 mL), and brine (10 mL) before drying over Na$_2$SO$_4$. The solvent was removed under reduced pressure and the residue was purified by flash column chromatography (hexanes:ethyl acetate, 8:1) affording 0.271 g of VI(a) (76%); $[\alpha]^{23}_D$ −26.14 (c 1.0, CHCl$_3$; R$_f$ 0.35 (hexanes:ethyl acetate, 4:1); IR (film) v 2986, 2930, 2894, 2856, 1598, 1489 cm$^{-1}$; $^1$H NMR (300 MHz, CDCl$_3$) δ: 7.78 (d, J=8.1 Hz, 2H), 7.29 (d, J=8.1 Hz, 2H), 6.65 (m, 3H), 6.51 (d, J=11.7 Hz, 1H), 5.97 (s, 2H), 5.54 (t, J=11.3 Hz, 1H), 4.43 (d, J=6, 1H), 3.85 (t, J=6.3, 1H), 3.61 (t, J=7.2 Hz), 3.18 (d, J=6.6, 1H), 2.91 (m, 2H), 2.44 (s, 3H), 1.52 (s, 3H), 1.33 (s, 3H), 0.79 (s, 9H), 0.02 (s, 3H), −0.04 (s, 3H) ppm; $^{13}$C NMR (150 MHz, CDCl$_3$) δ: 147.5, 146.6, 144.6, 134.7, 132.0, 130.3, 129.8, 129.7, 129.5, 128.5, 127.9, 122.5, 109.35, 109.0, 108.1, 100.9, 83.2, 78.0, 72.6, 71.8, 43.7, 39.9, 39.5, 30.1, 27.8, 25.8, 25.79, 25.75, 25.72, 25.51, 23.7, 21.7, 18.1, −4.3, −4.7 ppm; HRMS-EI Calcd for C$_{31}$H$_{41}$NO$_7$SSi: 599.2373. Found, 599.2376; Anal. calcd for C$_{31}$H$_{41}$NO$_7$SSi C, 62.28; H, 6.58. found C, 61.30; H, 6.63.

Example 3

N-[(1R,2aS,4aS,5S,5aR,12bR)-5-(tert-Butyl-dimethyl-silanyloxy)-3,3-dimethyl-1,2a,4a,5,5a,12b-hexahydro-phenanthro[2,3-d][1,3]dioxol-1-yl]4-methyl-benzenesulfonamide VII(a)

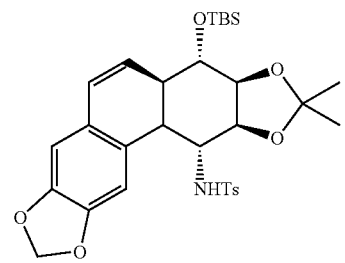

A flame-dried 25-mL flask was charged with olefin 13 (336 mg, 0.561 mmol) and silica gel which has been activate by heating under vacuum at 120° C. overnight (1.5 g). The starting materials were suspended in 10 mL freshly distilled methylene chloride and the solvent removed under reduced pressure. The silica gel supporting the absorbed reactants was heated externally at 120° C. under nitrogen atmosphere for 24 h, after which time the silica gel was loaded onto flash silica gel column and eluted with hexanes:ethyl acetate, 8:1-5:1 to give 175 mg (52%) of olefin VII(a) as a clear and colorless oil; $[\alpha]^{23}_D$ −123.7 (c 1.0, CHCl$_3$); R$_f$ 0.35 (hexanes:ethyl acetate, 2:1); IR (film) v 3268, 2929, 2887, 2857, 1598, 1503, 1485 cm$^{-1}$; $^1$H NMR (600 MHz, CDCl$_3$) δ: 7.43 (d, J=7 Hz, 2H), 7.13 (d, J=7 Hz, 2H), 6.49 (s, 2H), 6.34 (d, J=8 Hz, 1H), 5.95 (s, 1H), 5.86 (s, 1H), 5.76 (d, J=8 Hz, 1H), 4.51 (d, J=7 Hz, 1H), 4.28 (m, 1H), 4.11 (m, 1H), 3.99 (m, 1H), 3.79 (m, 1H), 2.82 (m, 1H), 2.62 (dd, J=11.1 Hz, J=5.4 Hz, 1H), 2.40 (s, 3H), 1.43 (s, 3H), 1.33 (s, 3H), 0.89 (s, 9H), 0.11 (s, 3H), 0.07 (s, 3H) ppm; $^{13}$C NMR (150 MHz, CDCl$_3$) δ: 146.7, 145.9, 142.1, 138.9, 128.9, 128.6, 127.7, 126.8, 126.3, 126.2, 110.4, 109.2, 107.0, 79.0, 78.3, 70.3, 54.1, 42.5, 41.5, 38.9, 27.8, 26.3, 25.7, 25.3, 22.7, 21.5, 18.0, −5.0, −5.0 ppm; HRMS-EI Calcd for C$_{31}$H$_{41}$NO$_7$SSi: 599.2373. Found, 599.2370; Anal. calcd for C$_{31}$H$_{41}$NO$_7$SSi C, 62.07; H, 6.89. found C, 62.16; H, 6.94.

Example 4

N-[(1R,2aS,4aS,5S,5aS,12bR)-5-(tert-Butyl-dimethyl-silanyloxy)-6-hydroxy-3,3-dimethyl-7-oxo-1,2a,4a,5,5a,6,7,12b-octahydro-phenanthro[2,3-d][1,3]dioxol-1-yl]4-methyl-benzenesulfonamide XI(a)

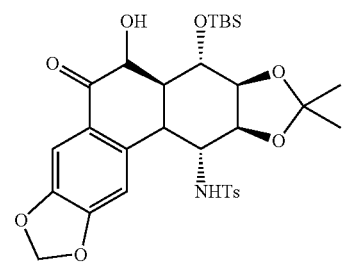

To a solution of olefin VII(a) (0.240 mg, 0.4 mmol) in methylene chloride (10 mL) was added 4-methylmorpholine N-oxide (58 mg, 0.48 mmol). The reaction mixture was allowed to stir for 10 minutes before the introduction of a single crystal of osmium tetroxide and two drops of water. The reaction was stirred until total consumption of starting material (10 h) before being quenched with a saturated solution of saturated sodium bisulfite (6 mL). The two layers were separated and the aqueous phase was extracted with ethyl acetate (3×30 mL). The organic phase was dried over sodium sulfate, filtered, and concentrated in vacuo to provide hydroxyketone XI(a) as a white crystalline solid (0.227 g, 89%) that was used without further purification; $R_f$ 0.42 (hexanes:ethyl acetate, 1:1); mp>200° C.; IR (film) v 3478, 3263, 2929, 2857, 1670, 1614, 1504, 1482, 1444, 1386, 1330, 1252, 1218, 1156, 1075, 1039 cm$^{-1}$; $^1$H NMR (600 MHz, CDCl$_3$) δ: 7.54 (d, J=7.8 Hz, 2H), 7.49, (s, 1H), 7.18 (d, J=7.8 Hz, 2H), 6.70 (s, 1H), 6.07 (s, 1H), 6.00 (s, 1H), 4.79 (d, J=8.7 Hz, 1H), 4.71 (m, 2H), 4.19 (m, 1H), 4.08 (m, 1H), 3.74 (m, 2H), 3.08 (dd, J=10.2 Hz, J=1.8 Hz, 1H), 2.45 (m, 1H), 2.41 (s, 3H), 1.36 (s, 3H), 1.31 (s, 3H), 0.87 (s, 9H), 0.12 (s, 3H), 0.07 (s, 3H) ppm; $^{13}$C NMR (150 MHz, CDCl$_3$) δ: 196.6, 152.5, 147.9, 142.6, 140.5, 138.9, 129.1, 126.9, 124.7, 111.2, 109.6, 106.9, 102.1, 78.9, 78.7, 70.3, 65.9, 57.9, 49.4, 39.7, 27.9, 25.7, 21.5, 17.95, −5.1 ppm; HRMS-EI Calcd for $C_{27}H_{32}NO_9SSi$ (M$^+$−57): 574.1567. Found: 574.1572.

Example 5

(3aS,3bR,10bR,11R,12S,12aS)-12-(tert-Butyl-dimethyl-silanyloxy)-2,2-dimethyl-5-oxo-4-(toluene-4-sulfonyl)-3a,3b,4,5,10b,11,12,12a-octahydro-1,3,7,9-tetraoxa-4-aza-dicyclopenta[a,h]phenanthrene-11-carbaldehyde II(a)

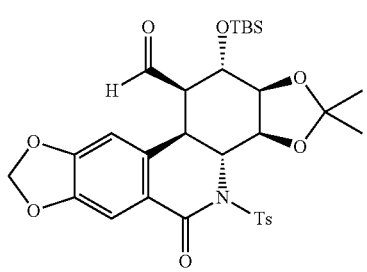

To a 10 mL round bottomed flask was added hydroxyl ketone XI(a) (0.4 g, 0.63 mmol) and 6 mL of a 1:1 mixture of ethanol:dioxane. The reaction flask was cooled externally in an ice bath and NaBH$_4$ (24 mg, 0.63 mmol) was added in one portion. The reaction was removed from the bath and allowed to warm to room temperature over 1 h. The reaction was quenched with 1 N HCl (4 mL) and separated. The aqueous phase was extracted with CH$_2$Cl$_2$ (3×20 mL) and the organic phase combined before drying over sodium sulfate. The crude mixture was concentrated in a 25 mL round bottomed flash and taken up in dioxane (8 mL). A stirring bar was added and the reaction was stirred while sodium periodate (0.332, 1.5 mmol) was added. The flask was covered to exclude light and H$_2$O (15 drops) added. The reaction was stirred until total consumption of starting material (23 h) as monitored by TLC. The reaction was quenched with H$_2$O (10 mL) and separated. The aqueous phase was extracted with CH$_2$Cl$_2$ (3×50 mL) and the combined organic phases dried over sodium sulfate. Concentration provided IX(a).

To a solution of hemi-aminal IX(a) (394 mg, 0.62 mmol) in N,N-Dimethylformamide (3 mL) was added 2-Iodoxybenzoic acid (520 mg, 1.86 mmol). After total consumption of starting material (by TLC), the reaction mixture was diluted with diethyl ether (200 mL) and washed sequentially with saturated aqueous sodium bisulfite (10 mL), sodium bicarbonate (3×10 mL), H$_2$O (10×1 mL), and brine (10 mL). The organic phase was dried over magnesium sulfate, filtered and concentrated. The final product was isolated by column chromatography (hexanes:ethyl acetate, 4:1). Yield: 225 mg, 61%, white solid; $R_f$ 0.31 (hexanes:ethyl acetate, 4:1); mp>200° C., recrystallized from hexanes/ethyl acetate 4:1; $[α]_D^{21}$+31.67 (c 0.5, CHCl$_3$); IR (film) v 2929, 2857, 1725, 1689, 1619, 1505, 1484, 1386, 1361, 1287, 1255, 1220, 1172, 1077, 1036 cm$^{-1}$; $^1$H NMR (600 MHz, CDCl$_3$) δ: 9.49 (s, 1H), 8.3 (d, J=8.2 Hz, 2H), 7.58 (s, 1H), 7.33 (d, J=8.2 Hz, 2H), 7.28 (s, 1H), 6.55 (s, 1H), 6.04 (d, J=5 Hz, 2H), 5.81 (dd, J=8.4 Hz, J=5.2 Hz, 1H), 4.79 (m, 1H), 4.50 (dd, J=12.7 Hz, J=8.4 Hz, 1H), 4.27 (dd, J=5.2 Hz, J=2.7 Hz, 1H), 3.83 (dd, J=12.6, J=4.0 Hz, 1H), 3.31 (m, 1H), 2.45 (s, 3H), 1.42 (s, 3H), 1.32 (s, 1H), 0.99 (s, 9H), 0.26 (s, 3H), 0.25 (s, 3H) ppm; $^{13}$C NMR (150 MHz, CDCl$_3$) δ: 196.2, 166.0, 153.0, 147.1, 143.9, 138.8, 137.0, 128.9, 128.8, 110.1, 109.4, 104.2, 102.2, 72.4, 66.6, 65.5, 55.6, 35.4, 31.0, 27.9, 26.9, 25.7, 22.7, 21.7, 18.1, 14.2, −4.7, −4.9 ppm; HRMS-EI Calcd for $C_{30}H_{36}NO_9SSi$ (M$^+$−15): 614.1879. Found: 614.1870; Anal. calcd for $C_{31}H_{39}NO_9SSi$ C, 59.12; H, 6.24. found C, 59.31; H, 6.29.

Example 6

(3aS,3bR,10bR,11R,12S,12aS)-12-(tert-Butyl-dimethyl-silanyloxy)-2,2-dimethyl-5-oxo-4-(toluene-4-sulfonyl)-3a,3b,4,5,10b,11,12,12a-octahydro-1,3,7,9-tetraoxa-4-aza-dicyclopenta[a,h]phenanthrene-11-carboxylic acid X(a)

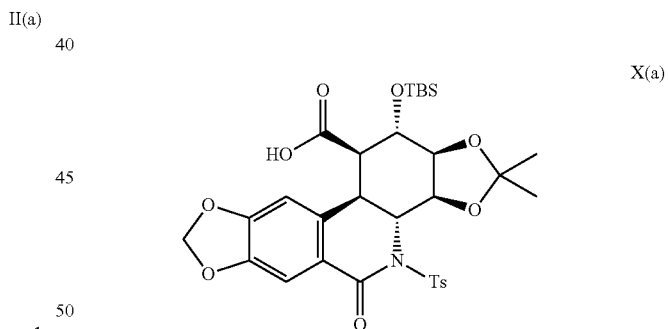

To a solution of aldehyde IX(a) (144 mg, 0.229 mmol) in dry methylene chloride (5 mL) was added sodium phosphate dibasic (81 mg, 0.57 mmol). The suspension was stirred while 3-chloroperbenzoic acid (130 mg, 0.57 mmol) was added. The reaction flask was sealed and heated at 40° C. overnight. The reaction mixture was diluted with methylene chloride (80 mL) and washed sequentially with saturated aqueous sodium bisulfite (10 mL), sodium bicarbonate (10 mL), and dried over sodium sulfate. The organic phase was filtered and concentrated in vacuo to provide carboxylic acid X(a) as a white crystalline solid (0.125 g, 85%) that was used without further purification; $R_f$ 0.1 (hexanes/ethyl acetate, 1:1); mp>200° C.; $[α]_D^{22}$−35.09 (c 1.25, CHCl$_3$); IR (KBr) v 3246, 2930, 2891, 2857, 1710, 1688, 1619, 1505, 1484, 1361, 1240, 1220, 1172, 1078, 1033 cm$^{-1}$; $^1$H NMR (300 MHz, CDCl$_3$) δ: 8.29 (d, J=8.3 Hz, 2H), 7.53 (s, 1H), 7.32 (d, J=8.3 Hz, 2H), 7.28 (s, 1H), 6.56 (s, 1H), 6.02 (d, J=3 Hz, 2H), 5.77 (dd, J=8.30 Hz, J=5.3 Hz, 1H), 4.85 (dd, J=12.5 Hz, J=8.4 Hz, 1H)), 4.84 (t, J=4.7 Hz, 1H), 4.22 (dd J=5.22, J=2.8 Hz, 1H), 3.76 (dd, J=12.4 Hz, J=4.1 Hz, 1H), 3.38 (t, J=3.5 Hz, 1H), 2.45 (s, 3H), 1.40 (s, 3H), 1.27 (s, 1H), 0.96 (s, 9H), 0.21 (s, 6H) ppm; $^{13}$C NMR (150 MHz, CDCl$_3$) δ: 174.3, 166.2, 152.8, 146.9, 143.8, 138.9, 137.7, 129.0, 128.8, 122.4, 109.8, 109.2, 103.4, 102.1, 72.8, 68.2, 64.9, 48.0, 35.5, 27.4, 26.9, 25.7, 21.7, 18.0, −4.9, −5.0 ppm; HRMS-EI Calcd for C$_{27}$H$_{30}$NO$_{10}$SSi (M$^+$−57): 588.1359. Found: 588.1354; Anal. calcd for C$_{31}$H$_{39}$NO$_{10}$SSi C, 57.65; H, 6.09. found C, 58.01; H, 6.37

Example 7

(3aS,3bR,10bR,11R,12S,12aS)-12-(tert-Butyl-dimethyl-silanyloxy)-2,2-dimethyl-5-oxo-4-(toluene-4-sulfonyl)-3a,3b, 4, 5, 10b,11,12,12a-octahydro-1,3,7, 9-tetraoxa-4-aza-dicyclopenta[a,h]phenanthrene-11-carboxylic acid methyl ester X(b)

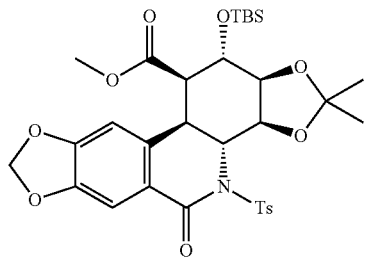

X(b)

To a solution of carboxylic acid X(a) (45 mg, 0.069 mmol) in diethyl ether (3 mL) was added freshly prepared diazomethane solution in diethyl ether until the persistence of yellow color and total consumption of starting material (by TLC). The reaction was quenched with one drop of acetic acid followed by saturated sodium bicarbonate solution (1 mL), diluted with diethyl ether (30 mL) and washed with saturated sodium bicarbonate solution (2×1 mL), dried over magnesium sulfate, filtered and concentrated. The crude reaction mixture was passed through short silica plug using hexane/ethyl acetate 1:1 as eluent and concentrated to provide methyl ester X(b) that was used without further purification. Yield: 38 mg, 83%, white crystalline solid; R$_f$ 0.45 (hexanes:ethyl acetate, 1:1); mp>200° C.; [α]$_D$$^{22}$−25.6809 (c 0.75, CHCl$_3$); IR (KBr) v 2986, 2953, 2931, 2896, 2858, 1739, 1692, 1620, 1598, 1505, 1485, 1361, 1289, 1264, 1173 cm$^{-1}$; $^1$H NMR (300 MHz, CDCl$_3$) δ: 8.30 (d, J=8.4 Hz, 2H), 7.55 (s, 1H), 7.32 (d, J=8.3 Hz, 2H), 6.58 (s, 1H), 6.02 (s, 2H), 5.78 (dd, J=8.30 Hz, J=5.4 Hz, 1H), 4.9 (dd, J=12.5 Hz, J=8.3 Hz, 1H), 4.78 (t, J=3.0 Hz, 1H), 4.24 (dd J=5.36 Hz, J=2.9 Hz, 1H), 3.79 (dd, J=12.4, J=4.2 Hz, 1H), 3.56 (s, 3H), 3.40 (t, J=3.7 Hz, 1H), 2.45 (s, 3H), 1.41 (s, 3H), 1.35 (s, 1H), 0.98 (s, 9H), 0.24 (s, 3H), 0.23 (s, 3H) ppm; $^{13}$C NMR (75 MHz, CDCl$_3$) δ: 169.4, 166.3, 152.8, 146.8, 143.7, 139.0, 138.2, 128.9, 128.8, 122.4, 109.8, 109.2, 103.5, 102.0, 72.9, 68.2, 65.2, 51.9, 48.1, 35.9, 27.5, 26.8, 25.7, 21.6, 18.0, −4.8, −4.9 ppm; HRMS-EI Calcd for C$_{28}$H$_{32}$NO$_{10}$SSi (M$^+$−57): 602.1516. Found: 602.1516.

Example 8

(3aS,3bR,10bR,11R,12S,12aS)-12-(tert-Butyl-dimethyl-silanyloxy)-2,2-dimethyl-5-oxo-3a,3b,4,5,10b, 11,12,12a-octahydro-1,3,7,9-tetraoxa-4-aza dicyclopenta[a,h]phenanthrene-11-carboxylic acid methyl ester X(c)

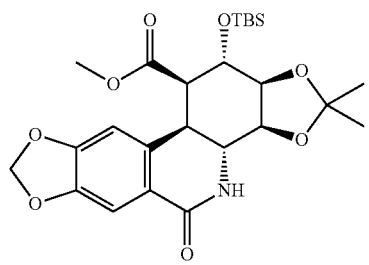

X(c)

To a solution of X(b) (52 mg, 0.079 mmol) in dry THF (1 mL) at −50° C. was added a 0.5 M solution of Na/naphthalene in DME until a green color persisted and total consumption of starting material was observed (by TLC). The solution was stirred for 10 minutes before the reaction was quenched with saturated aqueous ammonium chloride solution (1 mL). The reaction was warmed to room temperature and extracted with CH$_2$Cl$_2$ (6×15 mL). The combined organic phase was dried over sodium sulfate, filtered, and concentrated. The final product was isolated by column chromatography (hexanes:ethyl acetate, 5:1 to 2:1). Yield: 23 mg, 58%, clear oil; R$_f$ 0.28 (hexanes:ethyl acetate, 1:1); [α]$_D$$^{22}$−14.51 (c 0.50, CHCl$_3$); IR (film) v3320, 2952, 2930, 2895, 2857, 1743, 1669, 1619, 1504, 1484, 1460, 1385, 1369, 1321, 1288, 1260, 1222 cm$^{-1}$; $^1$H NMR (600 MHz, CDCl$_3$) δ: 7.62 (s, 1H), 6.56 (s, 1H), 6.02 (s, 2H), 5.96 (s, 1H), 4.86 (t, J=2.6, 1H), 4.41 (dd, J=13.6 Hz, J=8.2 Hz, 1H), 4.18 (dd, J=8.25 Hz, J=4.8 Hz, 1H), 4.11 (m, 1H), 3.66 (s, 3H), 3.40 (dd, J=13.6 Hz, J=3.7 Hz, 1H), 3.33 (m, 1H), 2.06 (s, 1H), 1.40 (s, 3H), 1.37 (s, 3H), 0.92 (s, 9H), 0.21 (s, 3H), 0.20 (s, 3H) ppm; $^{13}$C NMR (150 MHz, CDCl$_3$) δ: 169.6, 165.4, 151.4, 146.6, 135.4, 122.6, 110.5, 108.6, 103.3, 101.7, 69.2, 53.1, 51.9, 45.9, 33.4, 27.6, 26.5, 25.7, 17.9, −4.9, −5.0 ppm; HRMS-EI Calcd for C$_{25}$H$_{35}$NO$_8$Si (M$^+$): 505.2132. Found: 505.2131.

Example 9

(1R,2S,3R,4S,4aR,11bR)-2,3,4-Trihydroxy-6-oxo-1, 2,3,4,4a,5,6,11b-octahydro-[1,3]dioxolo[4,5-j] phenanthridine-1-carboxylic acid methyl ester I(a)

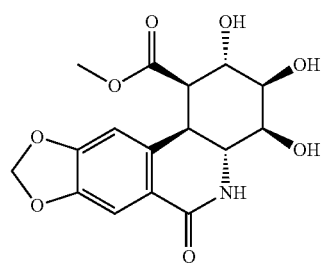

I(a)

To a solution of the detosylated methyl ester X(c) (23 mg, 0.046 mmol) in methanol (2 mL) was added 3% HCl in methanol (0.5 mL). The reaction mixture was stirred until total consumption of starting material (3 days). The solvent was removed under reduced pressure and the residue was purified by flash column chromatography using a 30:1 to 20:1 gradient of methylene chloride:methanol as eluent to provide methyl ester 19 (11 mg, 69%) as a white crystalline solid; mp>200° C. (methylene chloride:methanol); $R_f$ 0.06 (methylene chloride/methanol, 20:1); $[\alpha]_D^{22}$+24.53 (c 0.25,MeOH); IR (KBr) v 3311, 2913, 1732, 1648, 1609, 1497, 1462, 1349, 1259, 1037 cm$^{-1}$; $^1$H NMR (300 MHz, MeOD) δ: 7.33 (s, 1H), 6.59 (s, 1H), 5.93 (d, J=3.7, 2H), 4.50 (t, J=3.12, 1H), 4.21 (dd, J=13.1 Hz, J=10.1 Hz, 1H), 3.86 (m, 1H), 3.79, (dd, J=10.1, J=3.0, 1H), 3.51 (s, 3H), 3.39 (m, 1H), 3.29 (dd, J=13.1, J=4.1, 1H) ppm; $^{13}$C NMR (75 MHz, MeOD) δ: 170.8, 166.4, 151.7, 146.4, 137.3, 121.7, 106.9, 103.7, 101.8, 72.2, 71.9, 70.9, 51.4, 50.6, 44.8, 35.4 ppm; HRMS-FAB: (m/z) (M+H)$^+$: Calcd for C$_{16}$H$_{17}$NO$_8$: 352.1032. Found: 352.0941.

Example 10

(1R,2S,3R,4S,4aR,11bR)-2,3,4-Trihydroxy-6-oxo-1, 2,3,4,4a,5,6,11b-octahydro-[1,3]dioxolo[4,5-j] phenanthridine-1-carboxylic acid I(b)

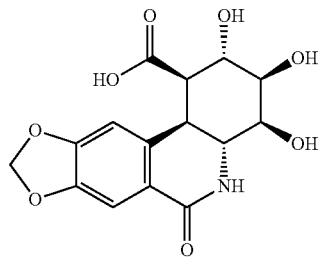

I(b)

To a solution of I(a) (6 mg, 0.017 mmol) in methanol (0.5 mL) was added LiOH (1 mg, 1.5 mmol). The reaction mixture was heated at 45° C. and stirred until total consumption of starting material (2 days) as monitored by TLC. The reaction was made slightly acidic with the addition of HCl (5 drops, 1 M) and concentrated to provide acid 20 (5 mg, 95%) as a white crystalline solid; mp>200° C.; $R_f$ 0.06 (methylene chloride:methanol, 4:1); IR (KBr) v 3412, 2920, 2115, 1641, 1505, 1471, 1409, 1462, 1363, 1267 cm$^{-1}$; $^1$H NMR (300 MHz, MeOD) δ: 7.41 (s, 1H), 6.72 (s, 1H), 6.02 (d, J=3.7, 2H), 4.64 (t, J=3.12, 1H), 4.35 (dd, J=13.1 Hz, J=10.1 Hz, 1H), 3.99 (m, 1H), 3.89, (dd, J=10.1, J=3.0, 1H), 3.45 (m, 1H), 3.38 (m, 1H) ppm; $^{13}$C NMR (75 MHz, MeOD) δ: 172.1, 166.4, 151.7, 146.4, 137.6, 121.7, 106.8, 103.8, 101.8, 72.4, 71.9, 71.1, 51.34, 45.03, 35.4 ppm.

Example 11

(3aS,3bR,10bR,11S,12S,12aS)-12-(tert-Butyl-dimethyl-silanyloxy)-11-hydroxymethyl-2,2-dimethyl-4-(toluene-4-sulfonyl)-3b,4,10b,11,12,12a-hexahydro-3aH-1,3,7,9-tetraoxa-4-aza-dicyclopenta[a,h]phenanthren-5-one X(d)

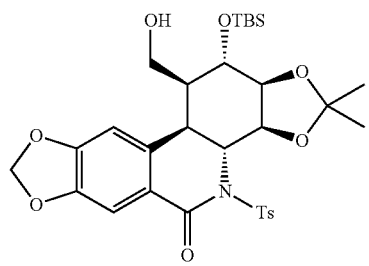

X(d)

To a solution of II(a) (175 mg, 0.278 mmol) in EtOH/dioxane (1:1, 5 mL) at 0° C. was added NaBH$_4$ (3 mg, 0.08 mmol). The reaction was allowed to warm to room temperature over 1.5 hours before being quenched with a solution of saturated NH$_4$Cl (1 mL). The EtOH/dioxane mixture was removed under reduced pressure and the aqueous residue was extracted with CH$_2$Cl$_2$ (3×25 mL). The organic phases were combined, dried over sodium sulfate, filtered, and concentrated to provide alcohol X(d) which was used without further purification. Yield: 150 mg, 85%, clear oil; $R_f$ 0.44 (hexanes:ethyl acetate, 1:1); $[\alpha]D^{22}$-47.72 (c 1.50, CHCl3); IR (film) v 3547, 2986, 2932, 2586, 1692, 1616, 1594, 1508, 1481, 1360 cm$^{-1}$; $^1$H NMR (300 MHz, CDCl3) δ: 8.28 (d, J=8.3 Hz, 2H), 7.54 (s, 1H), 7.30 (d, J=8.2 Hz, 2H), 6.77 (s, 1H), 6.04 (d, J=1.6 Hz, 2H), 5.65 (dd, J=8.8 Hz, J=5.6 Hz, 1H), 4.57 (d, J=1.8 Hz, 1H), 4.32 (d, J=4.6 Hz, 1H), 4.16 (dd J=12.8, J=8.9 Hz, 1H), 3.78 (m, 2H), 3.38 (dd, J=11.3 Hz, J=3.6 Hz, 1H), 2.55 (bs, 1H), 2.43 (s, 3H), 1.96 (bs, 1H), 1.43 (s, 3H), 1.35 (s, 3H), 0.96 (s, 9H), 0.20 (s, 6H) ppm; $^{13}$C NMR (75 MHz, CDCl3) δ: 166.4, 153.1, 147.1, 143.7, 138.9, 137.0, 129.0, 128.7, 123.2, 109.1, 108.7, 104.9, 102.1, 73.1, 67.3, 64.8, 60.0, 46.9, 37.4, 28.1, 26.3, 25.8, 21.6, 18.0, −4.8, −4.9 ppm; HRMS-EI Calcd for C$_{31}$H$_{41}$NO$_9$SSi (M+−15): 616.2032. Found: 616.2032.

Example 12

Acetic acid (3aS,3bR,10bR,11S,12S,12aS)-12-(tert-butyl-dimethyl-silanyloxy)-2,2-dimethyl-5-oxo-4-(toluene-4-sulfonyl)-3a,3b,4,5,10b,11,12,12a-octahydro-1,3,7,9-tetraoxa-4-aza-dicyclopenta[a,h]phenanthren-11-ylmethyl ester X(e)

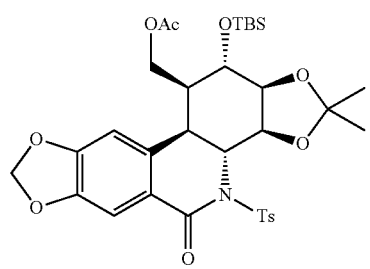

X(e)

To a solution of X(d) (150 mg, 0.237 mmol) in dry CH$_2$Cl$_2$ (10 mL) was added DMAP (1.5 mg, 0.012 mmol), followed by pyridine (0.1 mL, 1.187 mmol). Ac$_2$O (45 μL, 0.475 mmol) was added and the reaction was stirred for 1 hour before being quenched with saturated sodium bicarbonate (5 mL). The reaction was diluted with Et$_2$O (75 mL) and separated. The aqueous layer was extracted with Et$_2$O (2×75 mL) and the combined organic phases were washed with H$_2$O (10 mL), brine (10 mL), dried over magnesium sulfate, filtered, and concentrated. The final product was isolated by column chromatography using 5:1 mixture of hexanes:ethyl acetate as eluent. Yield: 128 mg, 81%, clear oil; R$_f$ 0.51 (hexanes/ethyl acetate, 1:1); [α]$_D^{22}$ −41.081 (c 3.0, CHCl$_3$); IR (film) v2988, 2952, 2930, 2858, 1742, 1694, 1619, 1598, 1505, 1485, 1395, 1362, 1254; $^1$H NMR (600 MHz, CDCl$_3$) δ: 8.29 (d, J=8.3 Hz, 2H), 7.54 (s, 1H), 7.31 (d, J=8.2 Hz, 2H), 6.84 (s, 1H), 6.03 (d, J=12.6 Hz, 2H), 5.62 (dd, J=8.7 Hz, J=5.6 Hz, 1H), 4.50 (s, 1H), 4.31 (d, J=5.3 Hz, 1H), 4.18 (t, J=11.1 Hz, 1H), 3.97 (dd, J=13.0 Hz, J=8.8 Hz, 1H), 3.85 (dd, J=11.0 Hz, J=3.6 Hz, 1H), 3.80 (dd, J=13.0, J=4.2, 1H), 2.7 (d, J=5.2, 1H), 2.44 (s, 3H), 2.03 (s, 3H), 1.42 (s, 3H), 1.36 (s, 3H), 0.96 (s, 9H), 0.19 (s, 1H); $^{13}$C NMR (150 MHz, CDCl3) δ: 170.7, 166.2, 153.2, 147.3, 143.8, 138.8, 136.2, 129.1, 128.7, 123.2, 108.9, 108.8, 105.0, 102.2, 78.4, 73.0, 66.3, 64.4, 60.8, 44.0, 37.0, 28.3, 26.2, 25.8, 25.78, 25.75, 25.6, 21.6, 20.8, 18.1, −4.8, −5.0; HRMS-EI Calcd for C$_{32}$H$_{40}$NO$_{10}$SSi (M$^+$−15): 658.2142. Found: 658.2152.

Example 13

((3aS,3bR,10bR,11S,12S,12aR)-12-hydroxy-2,2-dimethyl-5-oxo-3a,3b,4,5,10b,11,12,12a-octahydro-bis[1,3]dioxolo[4,5-c:4',5'-j]phenanthridin-11-yl)methyl acetate

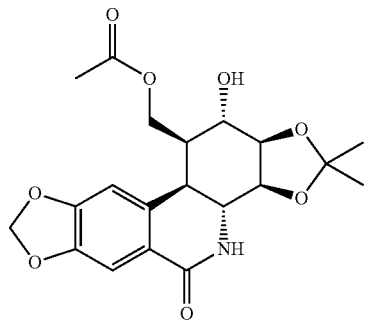 [SMILES: CC(=O)OC[C@H]1[C@H](O)[C@H]2OC(C)(C)O[C@H]2[C@@H]2NC(=O)c3cc4c(cc3[C@@H]12)OCO4]

To a solution of X(e) (137 mg, 0.203 mmol) in dry DME (5 mL) at −78° C. was added a 0.5 M solution of Na/naphthalene in DME until a green color persisted and total consumption of starting material was observed (by TLC). The solution was stirred for 10 minutes before the reaction was quenched with saturated aqueous ammonium chloride solution (2 mL). The reaction was warmed to room temperature, concentrated to remove DME, and extracted with CH$_2$Cl$_2$ (3×40 mL). The combined organic phase was dried over sodium sulfate, filtered, and concentrated. The resulting crude acetate was taken up in THF (2.5 mL) and cooled to 0° C. TBAF (0.1 mL, 1M in THF) was added dropwise over 2 minutes. The reaction was stirred until total consumption of starting material was observed (TLC) before the stirring bar was removed, silica (200 mg added), and the reaction concentrated to dryness. The final product was isolated by column chromatography using 1:1 mixture of hexanes:ethyl acetate as eluent. Yield: 61 mg, 74%, white solid; mp>200° C. R$_f$ 0.059 (hexanes/ethyl acetate, 1:1); [α]$_D^{22}$ −38.301 (c 1.35, DMSO); IR (film) v3303, 2982, 2922, 2901, 2853, 1734, 1655, 1652, 1612, 1483, 1459, 1364, 1246, 1235, 1215; $^1$H NMR (300 MHz, DMSO) δ: 7.76 (s, 1H), 7.35 (s, 1H), 7.03 (s, 1H) 6.09 (d, J=1.8, 2H), 5.48 (d, J=4.2, 1H), 4.35, (s, 1H), 4.24 (d, J=5.3, 1H), 4.19-4.10 (m, 3H), 3.46 (dd, J=14.0 Hz, J=8.2 Hz, 1H), 3.21 (dd, J=13.9 Hz, J=3.8 Hz, 1H), 2.80 (bs, 1H), 2.02 (s, 1H), 1.39 (s, 3H), 1.31 (s, 3H); $^{13}$C NMR (75 MHz, DMSO) δ: 170.9, 163.9, 151.3, 146.7, 134.5, 124.2, 108.9, 107.6, 105.4, 102.2, 77.9, 77.2, 65.3, 61.2, 53.5, 34.7, 28.3, 26.4, 21.2; HRMS-EI Calcd for C$_{20}$H$_{23}$NO$_8$ (M$^+$): 405.1424. Found: 405.1431.

Example 14

((1S,2S,3R,4S,4aR,11bR)-2,3,4-trihydroxy-6-oxo-1,2,3,4,4a,5,6,11b-octahydro-[1,3]dioxolo[4,5-j]phenanthridin-1-yl)methyl acetate I(c)

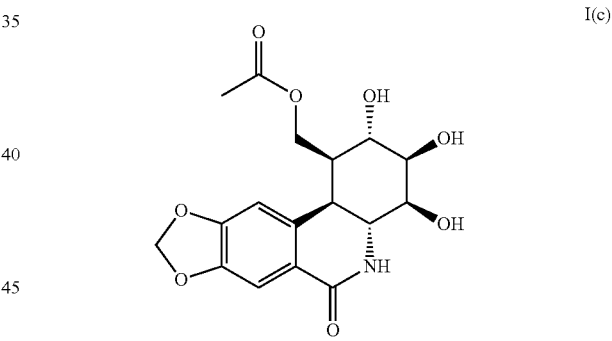

To a solution of the acetate of Example 13 (21 mg, 0.052 mmol) in MeOH (1 mL) was added an HCl solution (3% in MeOH, 3 mL). The reaction was stirred until total consumption of starting material as monitored by TLC (3 h) before being quenched to basic pH with saturated sodium bicarbonate solution. The crude reaction mixture was concentrated to dryness. The final product was isolated by column chromatography (methylene chloride:methanol, 5:1). Yield: 6 mg, 45%, white solid; mp>200° C.; R$_f$ 0.41 (methylene chloride:methanol, 5:1); [α]D$^{22}$ 97.32 (c 0.3, DMSO); $^1$H NMR (600 MHz, DMSO) δ: 7.36 (s, 1H), 7.01 (s, 1H), 6.76, (s, 1H), 6.10, (s, 2H), 5.14, (bs, 3H), 4.38 (t, J=10.7 Hz, 1H), 4.15-4.10 (m, 2H), 3.84 (s, 1H), 3.70 (dd J=9.8 Hz, J=2.9 Hz, 1H), 3.50 (dd J=13.2 Hz, J=9.9 Hz, 1H), 3.27 (dd J=13.3 Hz, J=4.0 Hz, 1H), 2.69 (bs, 1H), 2.03 (s, 3H) ppm; $^{13}$C NMR (150 MHz, DMSO) δ: 171.0, 164.1, 151.3, 146.6, 135.3, 123.8, 107.5, 105.5, 102.2, 73.1, 71.3, 69.1, 61.9, 51.6, 36.9, 21.3 ppm; HRMS-FAB Calcd for C$_{17}$H$_{20}$NO$_8$ (M+1): 366.0988. Found: 366.1088.

Example 15

(1S,2S,3R,4S,4aR,11bR)-2,3,4-trihydroxy-1-(hydroxymethyl)-1,2,3,4,4a, 5-hexahydro-[1,3]dioxolo[4,5-j]phenanthridin-6(11bH)-one I(d)

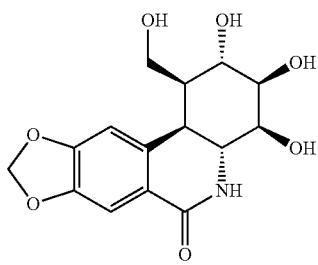

To a solution of acetate I(c) (25 mg, 0.062 mmol) at 0° C., in MeOH (5 mL) was added $K_2CO_3$ (40 mg, 0.62 mmol) and $H_2O$ (1 mL). The suspension was stirred until total consumption of starting material (TLC) before being quenched with HCl (4 drops, 6N). The reaction was allowed to warm to room temperature and stir (4 h). The pH of the reaction was made basic with the addition of saturated sodium bicarbonate solution and the methanol removed under reduced pressure. The resulting aqueous phase was concentrated overnight on a freeze-dryer. The salts were triturated with MeOH (5×5 mL) and the MeOH washes collected and concentrated. The final product was isolated by column chromatography (methylene chloride:methanol, 5:1). Yield: 15 mg, 75%, white solid; mp>200° C.; Rf 0.20 (methylene chloride:methanol, 5:1); $[\alpha]D^{22}$ 90.91 (c 0.25, DMSO); IR (film) v3361, 2916, 1646, 1608, 1503, 1460, 1385, 1361, 1252; $^1$H NMR (600 MHz, DMSO) δ: 7.34 (s, 1H), 6.97 (s, 1H), 6.66, (s, 1H), 6.09, (d, J=0.78, 2H), 5.04-4.97, (m, 3H), 4.47 (dd J=6.6 Hz, J=3.8 Hz, 1H), 4.19 (s, 1H), 3.89 (q, J=7.86 Hz, 1H), 3.82 (s, 1H), 3.69-3.64 (m, 1H), 3.42 (dd J=13.2 Hz, J=9.9 Hz, 1H), 3.39-3.32 (m, 1H), 3.15, (dd J=13.3 Hz, J=4.5 Hz, 1H), 2.41 (s, 1H) ppm; $^{13}$C NMR (150 MHz, DMSO) δ: 164.2, 151.2, 146.3, 136.3, 123.7, 107.4, 105.6, 102.1, 73.3, 71.6, 69.7, 57.8, 51.8, 44.4, 37.3 ppm; HRMS-FAB Calcd for $C_{15}H_{18}NO_7$ (M+1): 324.1085. Found: 324.1084.

Example 16

Anti-Cancer Activity (a) Cell Culture

The Human neuroblastoma (SH-SY5Y) and B-cell leukemia (Jurkat) cell lines were purchased from ATCC (Manassas, Va.). Cells were maintained and grown at 37° C., 95% humidity and 5% $CO_2$. Jurkat cells were grown with RPMI-1640 media (Sigma-Aldrich, Oakville, ON, Canada) supplemented with 10% fetal bovine serum (FBS) and 10 mg/ml Gentamycin (Gibco BRL, Mississauga, ON, Canada). SH-SY5Y cells were grown with Dulbecco's Modified Eagles Medium (DMEM) HAM F12 (Sigma-Aldrich), supplemented with 2 mM L-Glutamine, 10 mg/ml Gentamycin, and 10% FBS. Normal Human Fibroblasts (NHFs) obtained from Coriell Institute for Medical Research (New Jersey, USA) were cultured in Earle's Minimum Essential Medium (MEME) (Sigma Chemical Company, Mississauga, Ontario, Canada) completed with 15% fetal bovine serum, 2 mM L-Glutamine, 10 mg/ml Gentamycin, 1.5 g/l sodium bicarbonate, 1% vitamins, and essential (2%) and non-essential amino acids (1%) (Gibco BRL, VWR, Mississauga, ON, Canada).

Human non-small cell lung cancer line NCI-H460 (ATCC # HTB-177) and human pancreatic adenocarcinoma cancer cell line BxPC-3 (ATCC # CRL-1687) were cultured in RPMI-1640 medium supplemented with 10% fetal bovine serum (FBS) (Gibco, Carlsbad, Calif.), 100 mg/L penicillin G and 100 mg/L streptomycin and (Cellgro, Manassas, Va.). Human prostate carcinoma cells DU-145 (ATCC # HTB-81) were cultured in Dulbecco's modified Eagle Medium (Cellgro) supplemented with 10% FBS, 100 mg/L penicillin G and 100 mg/L streptomycin. Human mammary carcinoma cells MCF-7 (ATCC # HTB-22) were cultured using Dulbecco's modified Eagle Medium supplemented with 10% FBS, 100 mg/L penicillin G, 100 mg/L streptomycin, 1.0 mM Glutamax and 1.0 mM sodium pyruvate, (Gibco).

Peripheral blood was obtained from healthy non-smoking volunteers aged 25-50 years upon written and informed consent (University of Windsor REB #04-147). Whole blood samples were collected in BD Vacutainer™ Cell Preparation Tube and mononuclear cells were separated by density gradient centrifugation. The isolated cells were maintained in RPMI 1640 media supplemented and maintained as was the Jurkat culture.

(b) MTT Assay

To evaluate the cytotoxic effects of the C-1 derivatives of 7-deoxypancratistatin, mitochondrial dehydrogenase activities were measured. Jurkat and SH-SY5Y cells were grown and treated for 24, 48, and 72 hrs. Cells were treated with concentrations ranging from 0.25 to 10 μM of each derivative dissolved in DMSO Similarly, ncPBMCs and NHFs were treated to assess the effects of the C-1 derivatives on non-cancerous cells.

In addition, the BxPC-3, CRL-1687, DU-145 and MCF-7 lines were assessed by seeding 4×10³ cells per well into microplates. The cells were grown for 24 hrs before treatment at concentrations ranging from 0.01 to 10 μM and incubated for 48 hrs. MTT reagent (5 mg/mL, MP Biomedical, Solon, Ohio) was added to each well and incubated further for 2 hrs. The resulting formazan crystals were dissolved in DMSO and the OD was determined at a wavelength of 490 nm. The experiments were repeated at least twice for each compound per cell line. Cells treated with 0.1% DMSO were used as a control.

(c) Cellular Staining

Nuclear morphology was visualized using a final concentration of 10 μM of Hoechst 33342 dye (Molecular Probes, Eugene, Oreg., USA). Phosphatidyl serine flipping, (an apoptotic biochemical marker) was visualized with Annexin-V-FITC binding assay as per manufacturer's protocol (Molecular Probes, Eugene Oreg., USA). Cells were observed with a fluorescent microscope (Leica DM IRB, Germany); apoptotic indices were determined by counting brightly stained condensed nuclei (apoptotic cells) from at least 5 fields at 40× objective. Apoptotic cells were expressed as a percentage of the total number of cells counted. Standard error was calculated from at least 3 separate experiments.

(d) Results

Biological evaluation of C-1 derivatives. The novel C-1 analogues of 7-deoxypancratistatin of the present application were evaluated for antitumor activities in cancer cell lines in vitro. The hydroxymethyl analogue I(d) and its acetate I(c) displayed useful levels of activities. Therefore, to assess their potential, these two compounds were further evaluated for antiproliferative activities in a panel of human cancer cell lines as well as induction of apoptosis in human leukemia and neuroblastoma cells.

Cancer cell line growth inhibitory activities. Table 1 provides the antiproliferative potencies of compounds I(d) and I(c) along with pancratistatin (1) and 7-deoxypancratistatin (4). Although the C-1 analogues I(d) and I(c) provide antiproliferative potencies somewhat less than the natural pancratistatin, this fact is consistent with the overriding influence of the 7-hydroxyl phenolic functionality, present in 1, but not in I(d) and I(c). However, these compounds appear to be at least as good as or better than 7-deoxypancratistatin (4), pointing to the beneficial effect of the C-1 derivatization. Furthermore, it appears that large lipophilic C-1 substituents are more active.

Figure 2:
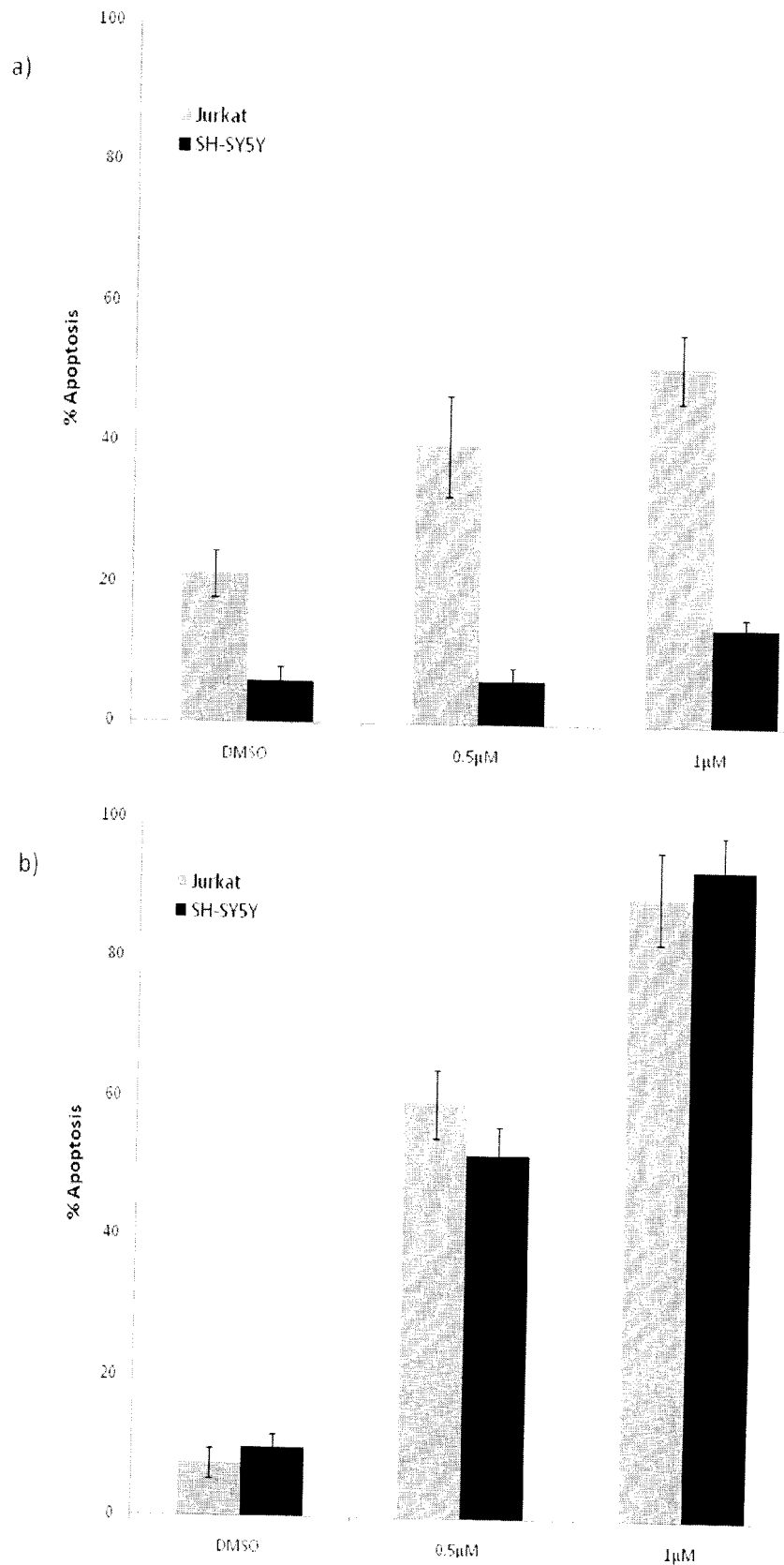
FIG. 2 shows that apoptosis is induced by compounds I(d) (a) and I(c) (b) in Jurkat and SH-SY5Y cells after 72 hrs exposure. Cells were stained with Hoechst dye and counted to determine the percentage of apoptotic cells; a minimum of 5 fields containing at least 100 cells per field was counted.
Figure 3:
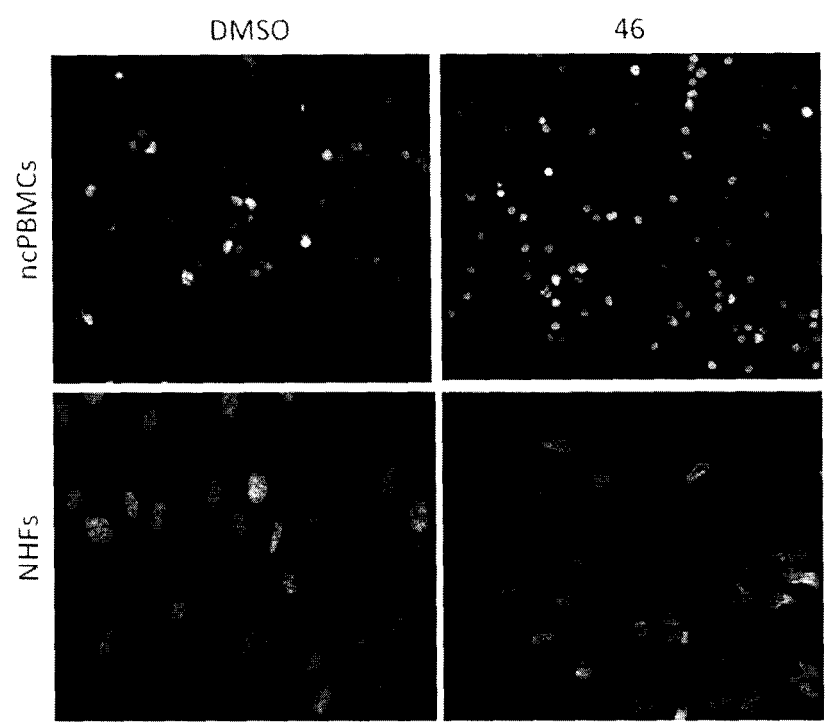
FIG. 3 shows that compound I(c) does not induce apoptosis in non-cancerous human cells. Naomal Human Fibroblasts (NHFs) and non-cancerous peripheral blood mononuclear cells (ncPBMC) were treated with compound I(c) and stained with Hoechst as described in the materials and methods. Apoptotic nuclear morphology is not visible in normal human fibroblasts (NHFs) or peripheral mono-nucleated blood cells (PMBC) prepared from blood obtained from healthy volunteers treatment with I(c).

Apoptosis induction. Apoptotic morphology was observed in Jurkat and SH-SY5Y cells after 72 hours treatment with compound I(d) or I(c) (FIG. 1) through Hoechst staining and Annexin-V binding. The effective dose at which 50% of cells were apoptotic (ED50) for compound I(d) in Jurkat cells was 1 µM and in SH-SY5Y cells was 10 µM. Compound I(c) had greater apoptotic efficacy than I(d) in both Jurkat and SH-SY5Y cells, as the $ED_{50}$ was determined to be 0.5 µM for both cell types (FIG. 2). This indicates that I(c), much like (1), has the ability to induce apoptosis specifically in cancerous cells. Most importantly, compound I(c) did not induce apoptosis in non-cancerous normal human cells such as normal human fibroblasts (NHFs) and peripheral mono-nucleated blood cells (PMBC) prepared from blood obtained from healthy volunteers (FIG. 3). These results indicate that compound I(c) is selectively targeting cancer cells to induce apoptosis, and could be a safer alternative to toxic chemotherapy.

TABLE 1

Inhibitory Activities: $IC_{50}$ (µg/mL)

| Compound | leukemia P388 | pancreas BxPC-3 | breast MCF-7 | CNS SF-268 | lung-NSC NCI-H460 | colon KM20L2 | prostate DU-145 | leukemia Jurkat | neuroblastoma Shsy5y |
|---|---|---|---|---|---|---|---|---|---|
| 1 | 0.039 | 0.028 | 0.032 | 0.017 | 0.048 | 0.062 | 0.016 | 0.163 | 0.163 |
| 4 | 0.44 | — | — | — | 0.29 | 0.22 | — | — | — |
| 1(d) | | 0.19 | 0.65 | | 0.09 | | 0.26 | 1.615 | 1.615 |
| 1(c) | | 0.11 | 0.29 | | 0.11 | | 0.37 | 0.183 | 0.183 |

That which is claimed is:

1. A compound of Formula I:

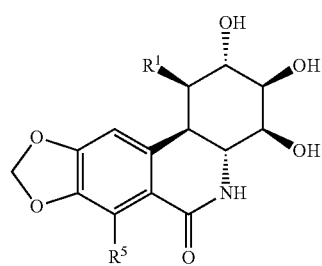

(I)

wherein:

$R^1$ is selected from $CH_2NR^2R^3$, $CH_2OR^2$, $CH_2OC(O)NR^2R^3$, $CH_2NHC(O)R^2$, $CH_2NHC(O)OR^2$, $CH_2CHC(O)NR^2R^3$, and $CH_2OC(O)R^2$; and $R^2$ and $R^3$ are independently selected from H, $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro;

$R^4$ is selected from $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro; and $R^5$ is selected from H and OH; and in each alkyl, alkenyl, cycloalkyl and aryl, one or more available H are optionally replaced with F, or a pharmaceutically acceptable salt, solvate or prodrug thereof.

2. The compound of claim 1, wherein $R^1$ is selected from $CH_2NH_2$, $CH_2OH$ and $CH_2OC(O)CH_3$.

3. A pharmaceutical composition comprising one or more compounds of Formula I of claim 1, and/or pharmaceutically acceptable salts, solvate and/or prodrugs thereof, and a pharmaceutically acceptable carrier.

4. A method of treating cancer comprising administering an effective amount of one or more compounds of Formula I and/or pharmaceutically acceptable salts, solvates and/or prodrugs thereof, to a subject in need thereof, the compound of Formula I being:

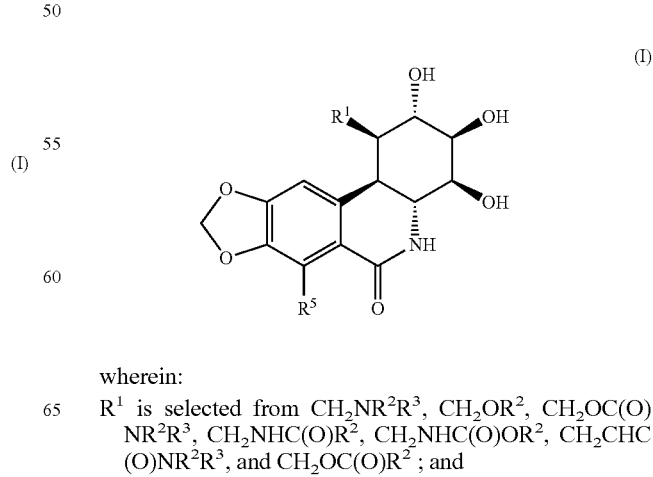

(I)

wherein:

$R^1$ is selected from $CH_2NR^2R^3$, $CH_2OR^2$, $CH_2OC(O)NR^2R^3$, $CH_2NHC(O)R^2$, $CH_2NHC(O)OR^2$, $CH_2CHC(O)NR^2R^3$, and $CH_2OC(O)R^2$; and $R^2$ and $R^3$ are independently selected from H, $C_{1-6}$alkyl, $C_{2-6}$alkenyl, $C_{3-10}$cycloalkyl and $C_{5-10}$aryl said latter four groups being unsubstituted or substituted with one to 5 groups independently selected from halo, OH, $OC_{1-4}$alkyl, $OC(O)C_{1-6}$alkyl and nitro;

$R^4$ is selected from $C_{1-6}$alkyl, $C_{2-6}$alkenyl, $C_{3-10}$cycloalkyl and $C_{6-10}$aryl said latter four groups being unsubstituted or substituted with one to 5 groups independently selected from halo, OH, $OC_{1-4}$alkyl, $OC(O)C_{1-6}$alkyl and nitro; and $R^5$ is selected from H and OH; and in each alkyl, alkenyl, cycloalkyl and aryl, one or more available H are optionally replaced with F.

5. The method of claim 4, wherein $R^1$ is selected from $CH_2NH_2$, $CH_2OH$ and $CH_2OC(O)CH_3$.

6. A process for preparing a compound of Formula II

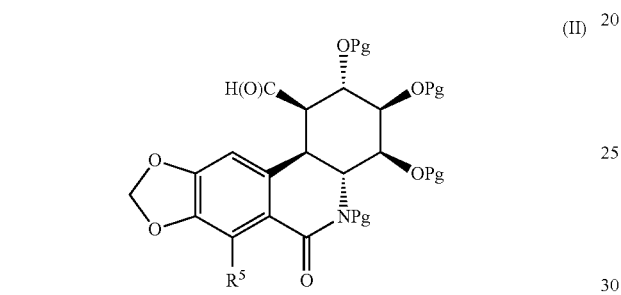

(II)

wherein $R^5$ is selected from H and OPg and each Pg may be the same or different and represent suitable protecting groups or any two adjacent Pg are joined to form a suitable cyclic protecting group;

the process comprising:

(i) reacting a compound of the Formula III with an aluminum acetylide derived from a compound of the Formula IV, followed by protection to form a compound of the Formula V, wherein $R^5$ and each Pg is as defined above:

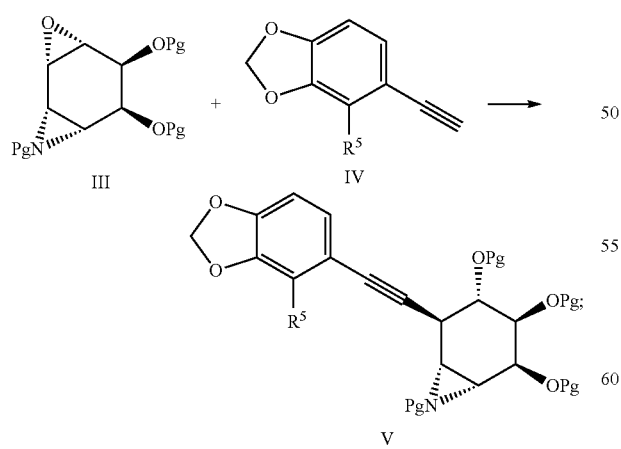

(ii) reducing the compound of Formula V to form a cis-alkene of the Formula VI, wherein $R^5$ and each Pg is as defined above:

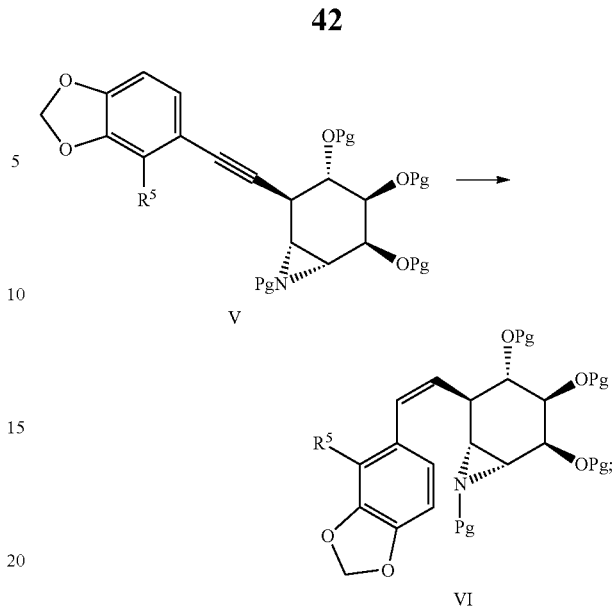

(iii) reacting the compound of the Formula VI under solid-state, silica gel catalysis conditions to form a compound of the Formula VII, wherein $R^5$ and each Pg is as defined above:

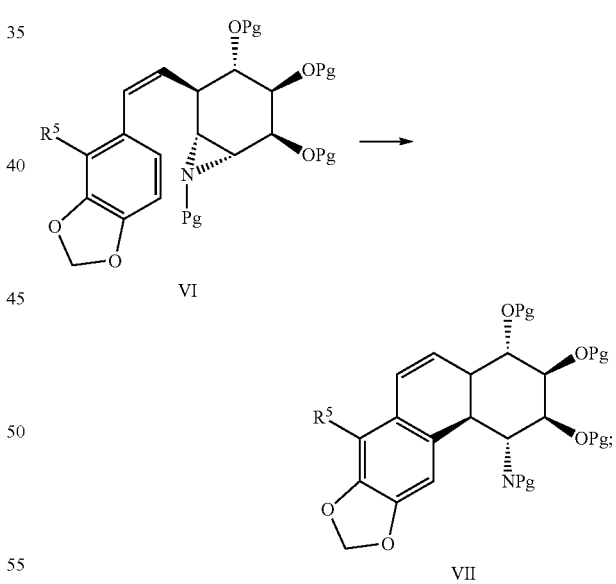

(iv) oxidatively cleaving the non-aromatic double bond in the compound of the Formula VII to form an intermediate diketone of the Formula VIII which cyclizes to form a compound of the Formula IX, wherein $R^5$ and each Pg is as defined above:

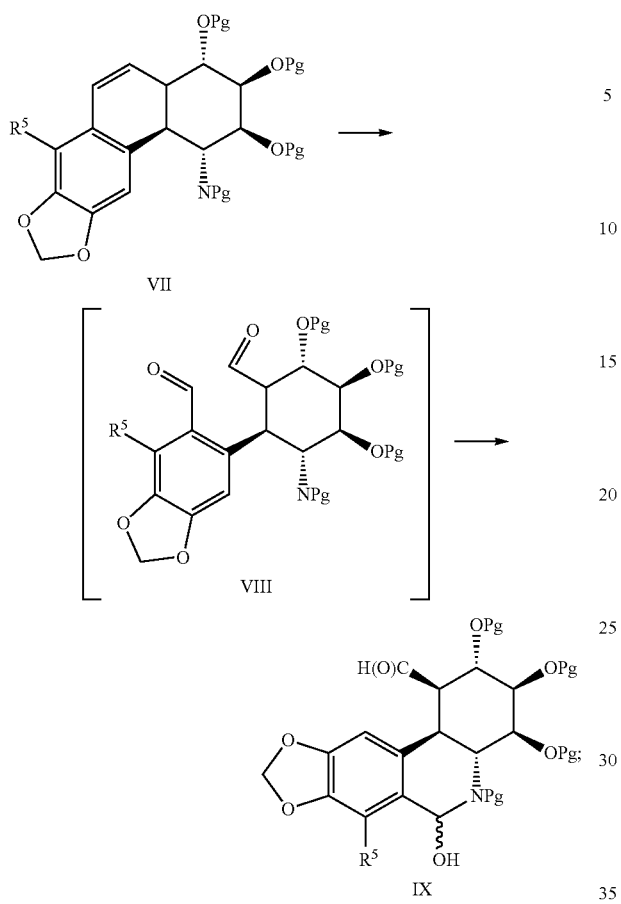

and (v) oxidizing the compound of the Formula IX to form a compound of Formula II, wherein $R^5$ and each Pg is as defined above:

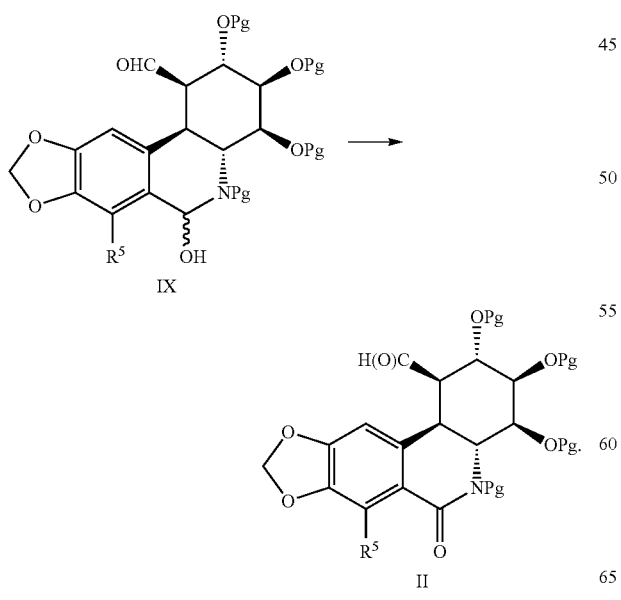

7. A process for preparing a compound of Formula I

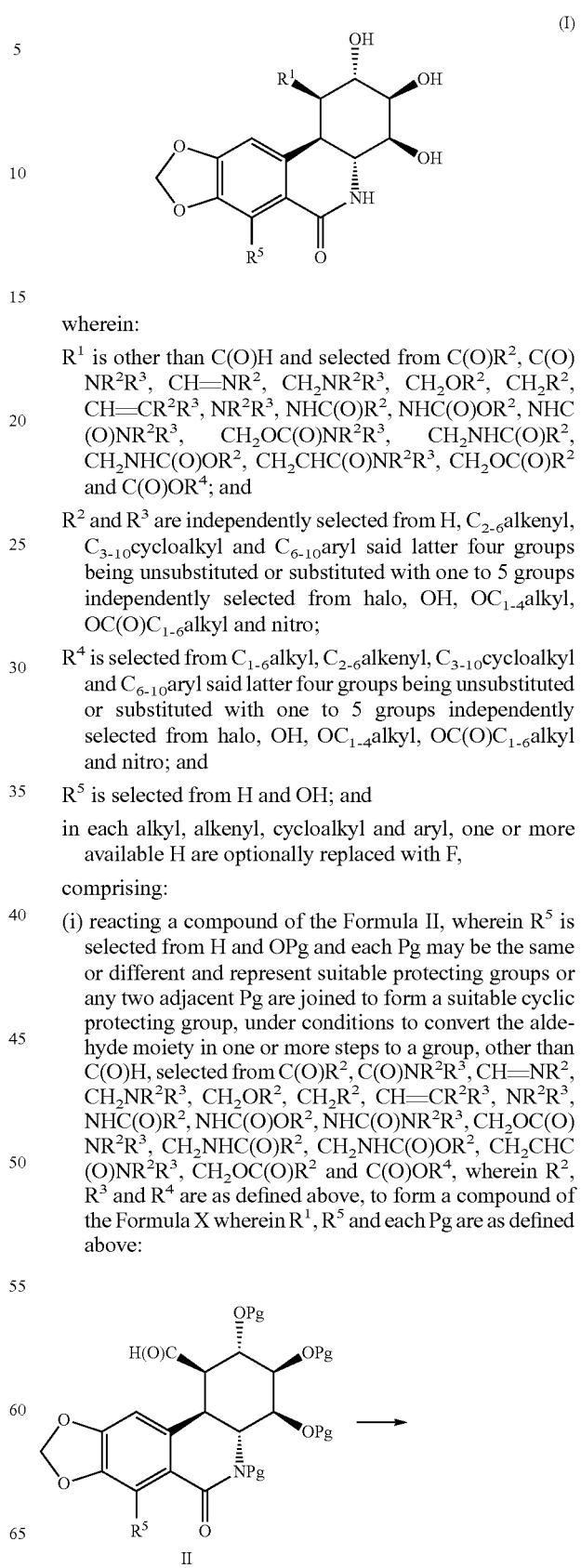

wherein:

$R^1$ is other than C(O)H and selected from C(O)$R^2$, C(O)NR$^2$R$^3$, CH=NR$^2$, CH$_2$NR$^2$R$^3$, CH$_2$OR$^2$, CH$_2$R$^2$, CH=CR$^2$R$^3$, NR$^2$R$^3$, NHC(O)R$^2$, NHC(O)OR$^2$, NHC(O)NR$^2$R$^3$, CH$_2$OC(O)NR$^2$R$^3$, CH$_2$NHC(O)R$^2$, CH$_2$NHC(O)OR$^2$, CH$_2$CHC(O)NR$^2$R$^3$, CH$_2$OC(O)R$^2$ and C(O)OR$^4$; and $R^2$ and $R^3$ are independently selected from H, C$_{2-6}$alkenyl, C$_{3-10}$cycloalkyl and C$_{6-10}$aryl said latter four groups being unsubstituted or substituted with one to 5 groups independently selected from halo, OH, OC$_{1-4}$alkyl, OC(O)C$_{1-6}$alkyl and nitro;

$R^4$ is selected from C$_{1-6}$alkyl, C$_{2-6}$alkenyl, C$_{3-10}$cycloalkyl and C$_{6-10}$aryl said latter four groups being unsubstituted or substituted with one to 5 groups independently selected from halo, OH, OC$_{1-4}$alkyl, OC(O)C$_{1-6}$alkyl and nitro; and $R^5$ is selected from H and OH; and in each alkyl, alkenyl, cycloalkyl and aryl, one or more available H are optionally replaced with F, comprising:

(i) reacting a compound of the Formula II, wherein $R^5$ is selected from H and OPg and each Pg may be the same or different and represent suitable protecting groups or any two adjacent Pg are joined to form a suitable cyclic protecting group, under conditions to convert the aldehyde moiety in one or more steps to a group, other than C(O)H, selected from C(O)R$^2$, C(O)NR$^2$R$^3$, CH=NR$^2$, CH$_2$NR$^2$R$^3$, CH$_2$OR$^2$, CH$_2$R$^2$, CH=CR$^2$R$^3$, NR$^2$R$^3$, NHC(O)R$^2$, NHC(O)OR$^2$, NHC(O)NR$^2$R$^3$, CH$_2$OC(O)NR$^2$R$^3$, CH$_2$NHC(O)R$^2$, CH$_2$NHC(O)OR$^2$, CH$_2$CHC(O)NR$^2$R$^3$, CH$_2$OC(O)R$^2$ and C(O)OR$^4$, wherein $R^2$, $R^3$ and $R^4$ are as defined above, to form a compound of the Formula X wherein $R^1$, $R^5$ and each Pg are as defined above:

-continued

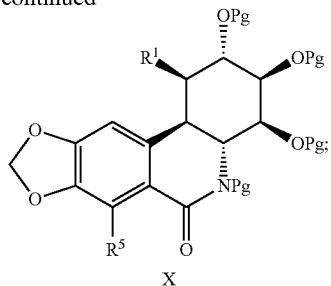

(ii) removing the Pg groups to form a compound of the Formula I wherein $R^1$ and $R^5$ are as defined above:

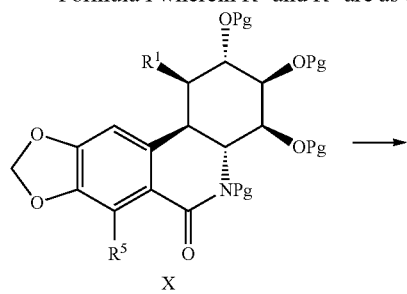

8. A process for preparing a compound of Formula I

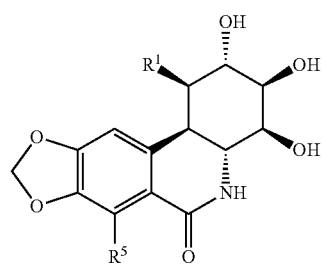

wherein $R^1$ is C(O)H and $R^5$ is H or OH, comprising removing the Pg groups from a compound of Formula II as defined in claim 5 to form the compound of the Formula I.

9. The compound of claim 1, wherein $R^1$ is selected from $CH_2OR^2$ and $CH_2OC(O)R^2$.

10. The compound of claim 9, wherein $R^2$ is selected from H, $C_{1-6}$alkyl and $C_{6-10}$aryl.

11. A compound of the Formula I(d):

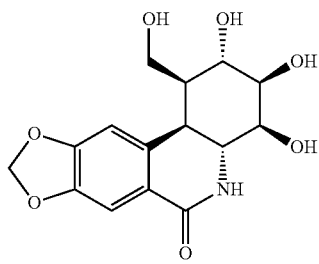 [SMILES: O=C1N[C@H]2[C@H](O)[C@H](O)[C@@H](O)[C@H](CO)[C@@H]2c2cc3c(cc21)OCO3]

or a pharmaceutically acceptable solvate or prodrug thereof.

12. A compound of the Formula I(c):

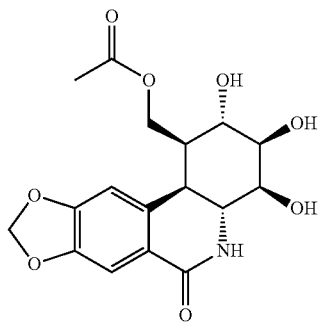 [SMILES: CC(=O)OC[C@H]1[C@H](O)[C@@H](O)[C@@H](O)[C@@H]2NC(=O)c3cc4c(cc3[C@@H]12)OCO4]

or a pharmaceutically acceptable solvate or prodrug thereof.

* * * * *

UNITED STATES PATENT AND TRADEMARK OFFICE
CERTIFICATE OF CORRECTION

PATENT NO.         : 8,703,792 B2                                    Page 1 of 1
APPLICATION NO.    : 13/140209
DATED              : April 22, 2014
INVENTOR(S)        : Tomas Hudlicky et al.

It is certified that error appears in the above-identified patent and that said Letters Patent is hereby corrected as shown below:

In the claims

1. Column 40, line 21, "or prodrug" should be deleted and the word "or" should be added before the word solvate.

2. Column 40, lines 28 and 33, "and/or prodrugs" should be deleted and the word "or" should be added before the word solvate.

3. Column 41, line 2, "$C_{5-10}$aryl", should be "$C_{6-10}$aryl".

4. Column 46, lines 28 and 49, "or prodrug" should be deleted and the word "or" should be added before the word solvate.

Signed and Sealed this
Second Day of August, 2016

Michelle K. Lee
*Director of the United States Patent and Trademark Office*